(12) United States Patent
Hogan et al.

(10) Patent No.: US 7,413,894 B2
(45) Date of Patent: Aug. 19, 2008

(54) TAG-1 AND TAG-2 PROTEINS AND USES THEREOF

(75) Inventors: Kevin T. Hogan, Charlottesville, VA (US); Craig L. Slingluff, Jr., Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 101 days.

(21) Appl. No.: 10/561,339

(22) PCT Filed: Jul. 1, 2004

(86) PCT No.: PCT/US2004/021168

§ 371 (c)(1),
(2), (4) Date: Dec. 19, 2005

(87) PCT Pub. No.: WO2005/005612

PCT Pub. Date: Jan. 20, 2005

(65) Prior Publication Data

US 2006/0140958 A1    Jun. 29, 2006

Related U.S. Application Data

(60) Provisional application No. 60/484,077, filed on Jul. 1, 2003.

(51) Int. Cl.
*C12N 15/63* (2006.01)
(52) U.S. Cl. .................. 435/320.1; 536/23.1; 536/24.3
(58) Field of Classification Search .............. 435/320.1; 536/23.1, 24.3
See application file for complete search history.

(56) References Cited

OTHER PUBLICATIONS

MPSRCH search result, 2007, 10.561.339.1.Oligo.rge, pp. 1-2.*

* cited by examiner

*Primary Examiner*—Larry R. Helms
*Assistant Examiner*—Minh-Tam Davis
(74) *Attorney, Agent, or Firm*—Rodney L. Sparks

(57) ABSTRACT

The present invention is directed to a newly discovered gene family with multiple isoforms, designated TAG-1, TAG-2a, TAG-2b, TAG-2c, and TAG-3, nucleic acid sequences encoding those proteins, and antibodies generated against said proteins. The genes, proteins, and peptides described herein may be used as diagnostic indicators of the presence of cancer and/or used in therapeutics to treat cancer.

3 Claims, 2 Drawing Sheets

*TAG-1*

```
CTCCACACCGCCTTGCAAGCTGAGGGAGCCGGCTCCGGCCTCTGCCAGCCCAGGAAGGGGCTCCCACAGTGCAGCGGCGG    80
                                      L  P  A  Q  E  G  A  P  T  V  Q  R  R
GCTGAAGGACTCCTCAAGTGCCACCAAAGTGGGAGCCCAGGCAGAGGAGGCGCCGAGAGCGAGCGAGGGCTGCCTGCCAG   160
 A  E  G  L  L  K  C  H  Q  S  G  S  P  G  R  G  G  A  E  S  E  R  G  L  P  A  S
CACGCTGTCACGTCTCAGCAATAGACTGCTCTTGAGGCTGGAGTGCAATGTTGTTATCATAGCTCACTGCAACCTGGAAC   240
   T  L  S  R  L  S  N  R  L  L  L  R  L  E  C  N  V  V  I  I  A  H  C  N  L  E
CCCTAGTCTCAAGAGATCCTCCAGCCTCAGCCTCCCTGGGATGGCTATTTTTGTTACTTCTGAATTCTACTACAAAAGAG   320
 P  L  V  S  R  D  P  P  A  S  A  S  L  G  W  L  F  L  L  L  L  N  S  T  T  K  E
TGCTGCAATAAAAATCTTTGAACAAGTTCTAATGCCGTTCAACTGGAATTGAAGTTTTCAATCGTTGGATATGTCAAAAT   400
 C  C  N  K  N  L  *
TTAATCAGATTGTATATTGCTCAATTACTTTCAAATTATGTACACCAAGTCATTCTTGCTCTGGCAAAATAAGAATATTT   480
TCATTAATATATCATTCAACTTGAAATTGCCCAGCTTTTCCTTCTCATTTCCCCCCAGTCAAATGAGTTGAATTAATACT   560
GTCTAAAAATATATATTCATTTGCTTACCTGTTAGTATTTGTTCCATGTATTAAGAAGCTTTGCTAGTATATGAAAATAT   640
ATGTATTACCATGTCTTGTGAATTAGTACTTTTATCATTTTGAAATGTTTGTTTTCATTTCTGCTGACCGTTCTAACCTG   720
GGTATCTATTTTGACTGGTTTTTAATGTAACTACTAACATCTTTTTATGTTCAGCACTTTTTCACAATTTTACTTTCAAT   800
GTCTTTATTTTTAAAATGTATCTTCTGTAGACAGTGTACAGGTGGTCTTGTTTTATTGTAAATCAAGTGACAATCTCTAT   880
TTCATAATTGACATATTTAATCCATATATATTTAATTTAATTGTTGTTATTTTGAGACTTAATATCCAGTTTTACTATTT   960
TGGCCCATTTATTTTTGGTTTATTTTAGATGTCTTGCCTTATCTTAGATTGATTGATATTTTTAGTATTTAATTACATTT  1040
CTTTTATAAATGTAATTTCTTGAATATTTGTTTTTTATTTAGCAATTGCTCTGGGAATATAAAATCATCTTTAAAATCT   1120
ATTTAGAGTTAATGGTACTACTTTATGCAGTAGGTAAAAACATTTCACTGCACAATTTCATTTGCAGGCACCTAACCTT   1200
CTGTGATAGTATTGTCTTATATTGTTATATTTATGAGATACAATCACTACAGTAAAATACTATTTTCTATTCATTGTGCC  1280
ATCTTATAAATAAACAGATGAATAAACAGATATTTTTGA                                          1319
```

*TAG-2a*

```
CTCCACACCGCCTTGCAAGCTGAGGGAGCCGGCTCCGGCCTCTGCCAGCCCAGGAAGGGGCTCCCACAGTGCAGCGGCGG    80
                                      L  P  A  Q  E  G  A  P  T  V  Q  R  R
GCTGAAGGACTCCTCAAGTGCCACCAAAGTGGGAGCCCAGGCAGAGGAGGCGCCGAGAGCGAGCGAGGGCTGCCTGCCAG   160
 A  E  G  L  L  K  C  H  Q  S  G  S  P  G  R  G  G  A  E  S  E  R  G  L  P  A  S
CACGCTGTCACGTCTCAGCAATAGACTGCTCTTGAGGCTGGAGTGCAATGTTGTTATCATAGCTCACTGCAACCTGGAAC   240
   T  L  S  R  L  S  N  R  L  L  L  R  L  E  C  N  V  V  I  I  A  H  C  N  L  E
CCCTAGTCTCAAGAGATCCTCCAGCCTCAGCCTCCCTGTTCCAGGATACATGTGCAGGATGTGCAAGTTTGCTACATGGG   320
 P  L  V  S  R  D  P  P  A  S  A  S  L  F  Q  D  T  C  A  G  C  A  S  L  L  H  G
TAAATATGTGCCATGGCAGTTTGCTGCATCTATTAACCCATTACCTAGGTATTAAGCCCGATACAAGAGTTATGGAAAAG   400
 *
CTGCACTCTTCTACTTCCAAAGTTTAACTTCTTCACAGAAGTCAGTTTCAGAGTTGAGAAAAGCAAATACTTGCTACATA   480
TTTTGAGGAACAATAAGTATTGAAGTTGCAAACAGGTTCTATGGATATTTGTCAACAGAAGATAGCTGATCACAAATGCG   560
CAGAGAGGTAGAAAAATGACACAATGACCACCCTACCCTCTGAGTCAGCAAATTGTTTTCTCAGTACATTTCTACTCTGG   640
TCCTTGTTTAATAAAACCTCTTTCTCCTTA                                                     670
```

*TAG-2b*

```
CTCCACACCGCCTTGCAAGCTGAGGGAGCCGGCTCCGGCCTCTGCCAGCCCAGGAAGGGGCTCCCACAGTGCAGCGGCGG    80
                                      L  P  A  Q  E  G  A  P  T  V  Q  R  R
GCTGAAGGACTCCTCAAGTGCCACCAAAGTGGGAGCCCAGGCAGAGGAGGCGCCGAGAGCGAGCGAGGGCTGCCTGCCAG   160
 A  E  G  L  L  K  C  H  Q  S  G  S  P  G  R  G  G  A  E  S  E  R  G  L  P  A  S
CACGCTGTCACGTCTCAGCAATAGACTGCTCTTGAGGCTGGAGTGCAATGTTGTTATCATAGCTCACTGCAACCTGGAAC   240
   T  L  S  R  L  S  N  R  L  L  L  R  L  E  C  N  V  V  I  I  A  H  C  N  L  E
CCCTAGTCTCAAGAGATCCTCCAGCCTCAGCCTCCCTGTTCCAGGATACATGTGCAGGATGTGCAAGTTTGCTACATGGG   320
 P  L  V  S  R  D  P  P  A  S  A  S  L  F  Q  D  T  C  A  G  C  A  S  L  L  H  G
TAAATATGTGCCATGGCAGTTTGCTGCATCTATTAACCCATTACCTAGGTATTAAGCCCGGAAATAAGAATGGCAGAAAA   400
 *
TGTGAAGAGTTATTGTGTGGGGAAGTGGCCTCTACATAGAAATGTTTTTCCACTGAATGTTCCTGTTGTGCTGATGAACA   480
AAGGAGTTCATCACAGGCCAGAAACTAAGATAGATAGATAAATAAATAAATAAATAAATAA                       541
```

*TAG-2c*

```
CTCCACACCGCCTTGCAAGCTGAGGGAGCCGGCTCCGGCCTCTGCCAGCCCAGGAAGGGGCTCCCACAGTGCAGCGGCGG    80
                                      L  P  A  Q  E  G  A  P  T  V  Q  R  R
GCTGAAGGACTCCTCAAGTGCCACCAAAGTGGGAGCCCAGGCAGAGGAGGCGCCGAGAGCGAGCGAGGGCTGCCTGCCAG   160
 A  E  G  L  L  K  C  H  Q  S  G  S  P  G  R  G  G  A  E  S  E  R  G  L  P  A  S
CACGCTGTCACGTCTCAGCAATAGACTGCTCTTGAGGCTGGAGTGCAATGTTGTTATCATAGCTCACTGCAACCTGGAAC   240
   T  L  S  R  L  S  N  R  L  L  L  R  L  E  C  N  V  V  I  I  A  H  C  N  L  E
CCCTAGTCTCAAGAGATCCTCCAGCCTCAGCCTCCCTGTTCCAGGATACATGTGCAGGATGTGCAAGTTTGCTACATGGG   320
 P  L  V  S  R  D  P  P  A  S  A  S  L  F  Q  D  T  C  A  G  C  A  S  L  L  H  G
TAAATATGTGCCATGGCAGTTTGCTGCATCTATTAACCCATTACCTAGGTATTAAGCCCGATCCCAGAAAACCTGCAGAG   400
 *
AGAAGCAGCAGCTGGACCTCGGGATGACTATGGCTGGACGTCAGGAGAGAAGCAGTTTGACTTCAGAGGGACAGCTTGAT   480
GGTGTAACTTCAGAGAAGAATCTGGTTAGAGATGGCTAGACTCCAGGAAAAGATTACCTACCCTTCCCCTACCCTTTTCT   560
CAGCTCCCCTTCCCACTGAGAGCCACTTTCACCGCAATAAAAATCCCCCACATGCACTATCCTTC                 624
```

FIG. 1

SEQUENCE LISTING

<160> NUMBER OF SEQ ID NOS: 46

<210> SEQ ID NO 1
<211> LENGTH: 1319
<212> TYPE: DNA

<213> ORGANISM: Homo sapiens

<400> SEQUENCE: 1

| | | | | | |
|---|---|---|---|---|---|
| ctccacaccg | ccttgcaagc | tgagggagcc | ggctccggcc | tctgccagcc | caggaagggg | 60 |
| ctcccacagt | gcagcggcgg | gctgaaggac | tcctcaagtg | ccaccaaagt | gggagcccag | 120 |
| gcagaggagg | cgccgagagc | gagcgagggc | tgcctgccag | cacgctgtca | cgtctcagca | 180 |
| atagactgct | cttgaggctg | gagtgcaatg | ttgttatcat | agctcactgc | aacctggaac | 240 |
| ccctagtctc | aagagatcct | ccagcctcag | cctccctggg | atggctattt | ttgttacttc | 300 |
| tgaattctac | tacaaaagag | tgctgcaata | aaaatctttg | aacaagttct | aatgccgttc | 360 |
| aactggaatt | gaagttttca | atcgttggat | atgtcaaaat | ttaatcagat | tgtatattgc | 420 |
| tcaattactt | tcaaattatg | tacaccaagt | cattcttgct | ctggcaaaat | aagaatattt | 480 |
| tcattaatat | atcattcaac | ttgaaattgc | ccagcttttc | cttctcattt | cccccagtc | 540 |
| aaatgagttg | aattaatact | gtctaaaaat | atatattcat | ttgcttacct | gttagtattt | 600 |
| gttccatgta | ttaagaagct | ttgctagtat | atgaaaatat | atgtattacc | atgtcttgtg | 660 |
| aattagtact | tttatcattt | tgaaatgttt | gttttcattt | ctgctgaccg | ttctaacctg | 720 |
| ggtatctatt | ttgactggtt | tttaatgtaa | ctactaacat | ctttttatgt | tcagcacttt | 780 |
| ttcacaattt | tactttcaat | gtctttattt | ttaaaatgta | tcttctgtag | acagtgtaca | 840 |
| ggtggtcttg | ttttattgta | aatcaagtga | caatctctat | ttcataattg | acatatttaa | 900 |
| tccatatata | tttaatttaa | ttgttgttat | tttgagactt | aatatccagt | tttactattt | 960 |
| tggcccattt | attttggtt | tattttagat | gtcttgcctt | atcttagatt | gattgatatt | 1020 |
| tttagtattt | aattacattt | cttttataaa | tgtaatttct | tgaatatttg | tttttatttt | 1080 |
| agcaattgct | ctgggaatat | aaaaatcatc | tttaaaatct | atttagagtt | aatggtacta | 1140 |
| ctttatgcag | taggtaaaaa | catttccacta | gcacaatttc | atttgcaggc | acctaacctt | 1200 |
| ctgtgatagt | attgtcttat | attgttatat | ttatgagata | caatcactac | agtaaaatac | 1260 |
| tattttctat | tcattgtgcc | atcttataaa | taaacagatg | aataaacaga | tatttttga | 1319 |

<210> SEQ ID NO 2
<211> LENGTH: 670
<212> TYPE: DNA
<213> ORGANISM: Homo sapiens

<400> SEQUENCE: 2

| | | | | | |
|---|---|---|---|---|---|
| ctccacaccg | ccttgcaagc | tgagggagcc | ggctccggcc | tctgccagcc | caggaagggg | 60 |
| ctcccacagt | gcagcggcgg | gctgaaggac | tcctcaagtg | ccaccaaagt | gggagcccag | 120 |
| gcagaggagg | cgccgagagc | gagcgagggc | tgcctgccag | cacgctgtca | cgtctcagca | 180 |
| atagactgct | cttgaggctg | gagtgcaatg | ttgttatcat | agctcactgc | aacctggaac | 240 |
| ccctagtctc | aagagatcct | ccagcctcag | cctccctgtt | ccaggataca | tgtgcaggat | 300 |
| gtgcaagttt | gctacatggg | taaatatgtg | ccatggcagt | tgctgcatc | tattaaccca | 360 |
| ttacctaggt | attaagcccg | atacaagagt | tatggaaaag | ctgcactctt | ctacttccaa | 420 |
| agtttaactt | cttcacagaa | gtcagtttca | gagttgagaa | agcaaatac | ttgctacata | 480 |
| ttttgaggaa | caataagtat | tgaagttgca | acaggttct | atggatattt | gtcaacagaa | 540 |
| gatagctgat | cacaaatgcg | cagagaggta | gaaaaatgac | acaatgacca | ccctaccctc | 600 |
| tgagtcagca | aattgttttc | tcagtacatt | tctactctgg | tccttgttta | ataaaacctc | 660 |
| tttctcctta | | | | | | 670 |

<210> SEQ ID NO 3
<211> LENGTH: 541
<212> TYPE: DNA
<213> ORGANISM: Homo sapiens

<400> SEQUENCE: 3

| | | | | | |
|---|---|---|---|---|---|
| ctccacaccg | ccttgcaagc | tgagggagcc | ggctccggcc | tctgccagcc | caggaagggg | 60 |
| ctcccacagt | gcagcggcgg | gctgaaggac | tcctcaagtg | ccaccaaagt | gggagcccag | 120 |
| gcagaggagg | cgccgagagc | gagcgagggc | tgcctgccag | cacgctgtca | cgtctcagca | 180 |
| atagactgct | cttgaggctg | gagtgcaatg | ttgttatcat | agctcactgc | aacctggaac | 240 |
| ccctagtctc | aagagatcct | ccagcctcag | cctccctgtt | ccaggataca | tgtgcaggat | 300 |
| gtgcaagttt | gctacatggg | taaatatgtg | ccatggcagt | ttgctgcatc | tattaaccca | 360 |
| ttacctaggt | attaagcccg | aaataagaa | tggcagaaaa | tgtgaagagt | tattgtgtgg | 420 |
| ggaagtggcc | tctacataga | aatgttttc | cactgaatgt | tcctgttgtg | ctgatgaaca | 480 |
| aaggagttca | tcacaggcca | gaaactaaga | tagatagata | aataaataaa | taaataaata | 540 |
| a | | | | | | 541 |

<210> SEQ ID NO 4
<211> LENGTH: 624
<212> TYPE: DNA
<213> ORGANISM: Homo sapiens

<400> SEQUENCE: 4

| | | | | | |
|---|---|---|---|---|---|
| ctccacaccg | ccttgcaagc | tgagggagcc | ggctccggcc | tctgccagcc | caggaagggg | 60 |
| ctcccacagt | gcagcggcgg | gctgaaggac | tcctcaagtg | ccaccaaagt | gggagcccag | 120 |
| gcagaggagg | cgccgagagc | gagcgagggc | tgcctgccag | cacgctgtca | cgtctcagca | 180 |
| atagactgct | cttgaggctg | gagtgcaatg | ttgttatcat | agctcactgc | aacctggaac | 240 |
| ccctagtctc | aagagatcct | ccagcctcag | cctccctgtt | ccaggataca | tgtgcaggat | 300 |
| gtgcaagttt | gctacatggg | taaatatgtg | ccatggcagt | ttgctgcatc | tattaaccca | 360 |
| ttacctaggt | attaagcccg | atcccagaaa | acctgcagag | agaagcagca | gctggacctc | 420 |
| gggatgacta | tggctggacg | tcaggagaga | agcagtttga | cttcagaggg | acagcttgat | 480 |
| ggtgtaactt | cagagaagaa | tctggttaga | gatggctaga | ctccaggaaa | agattaccta | 540 |
| cccttcccct | acccttttct | cagctcccct | tcccactgag | agccactttc | accgcaataa | 600 |
| aatcccccac | atgcactatc | cttc | | | | 624 |

<210> SEQ ID NO 5
<211> LENGTH: 542
<212> TYPE: DNA
<213> ORGANISM: Homo sapiens

<400> SEQUENCE: 5

| | | | | | |
|---|---|---|---|---|---|
| ctccacaccg | ccttgcaagc | tgagggagcc | ggctccggcc | tctgccagcc | caggaagggg | 60 |
| ctcccacagt | gcagcggcgg | gctgaaggac | tcctcaagtg | ccaccaaagt | gggagcccag | 120 |
| gcagaggagg | cgccgagagc | gagcgagggc | tgcctgccag | cacgctgtca | cgtctcagca | 180 |
| atagactgct | cttgagttcc | aggatacatg | tgcaggatgt | gcaagtttgc | tacatgggta | 240 |
| aatatgtgcc | atggcagttt | gctgcatcta | ttaacccatt | acctaggtat | taagcccgat | 300 |
| cccagaaaac | ctgcagagag | aagcagcagc | tggacctcgg | gatgactatg | gctggacgtc | 360 |

```
aggagagaag cagtttgact tcagagggac agcttgatgg tgtaacttca gagaagaatc    420
tggttagaga tggctagact ccaggaaaag attacctacc cttcccctac ccttttctca    480
gctccccttc ccactgagag ccactttcac cgcaataaaa tcccccacat gcactatcct    540
tc                                                                   542
```

```
<210> SEQ ID NO 6
<211> LENGTH: 99
<212> TYPE: PRT
<213> ORGANISM: Homo sapiens

<400> SEQUENCE: 6

Leu Pro Ala Gln Glu Gly Ala Pro Thr Val Gln Arg Arg Ala Glu Gly
1               5                   10                  15

Leu Leu Lys Cys His Gln Ser Gly Ser Pro Gly Arg Gly Gly Ala Glu
                20                  25                  30

Ser Glu Arg Gly Leu Pro Ala Ser Thr Leu Ser Arg Leu Ser Asn Arg
            35                  40                  45

Leu Leu Leu Arg Leu Glu Cys Asn Val Val Ile Ile Ala His Cys Asn
50                  55                  60

Leu Glu Pro Leu Val Ser Arg Asp Pro Pro Ala Ser Ala Ser Leu Gly
65                  70                  75                  80

Trp Leu Phe Leu Leu Leu Leu Asn Ser Thr Thr Lys Glu Cys Cys Asn
                85                  90                  95

Lys Asn Leu

<210> SEQ ID NO 7
<211> LENGTH: 63
<212> TYPE: PRT
<213> ORGANISM: Homo sapiens

<400> SEQUENCE: 7

Leu Pro Ala Ser Thr Leu Ser Arg Leu Ser Asn Arg Leu Leu Leu Arg
1               5                   10                  15

Leu Glu Cys Asn Val Val Ile Ile Ala His Cys Asn Leu Glu Pro Leu
                20                  25                  30

Val Ser Arg Asp Pro Pro Ala Ser Ala Ser Leu Gly Trp Leu Phe Leu
            35                  40                  45

Leu Leu Leu Asn Ser Thr Thr Lys Glu Cys Cys Asn Lys Asn Leu
50                  55                  60

<210> SEQ ID NO 8
<211> LENGTH: 59
<212> TYPE: PRT
<213> ORGANISM: Homo sapiens

<400> SEQUENCE: 8

Thr Leu Ser Arg Leu Ser Asn Arg Leu Leu Leu Arg Leu Glu Cys Asn
1               5                   10                  15

Val Val Ile Ile Ala His Cys Asn Leu Glu Pro Leu Val Ser Arg Asp
                20                  25                  30

Pro Pro Ala Ser Ala Ser Leu Gly Trp Leu Phe Leu Leu Leu Leu Asn
            35                  40                  45

Ser Thr Thr Lys Glu Cys Cys Asn Lys Asn Leu
50                  55

<210> SEQ ID NO 9
<211> LENGTH: 93
```

```
<212> TYPE: PRT
<213> ORGANISM: Homo sapiens

<400> SEQUENCE: 9

Leu Pro Ala Gln Glu Gly Ala Pro Thr Val Gln Arg Arg Ala Glu Gly
1               5                   10                  15

Leu Leu Lys Cys His Gln Ser Gly Ser Pro Gly Arg Gly Gly Ala Glu
            20                  25                  30

Ser Glu Arg Gly Leu Pro Ala Ser Thr Leu Ser Arg Leu Ser Asn Arg
        35                  40                  45

Leu Leu Leu Arg Leu Glu Cys Asn Val Val Ile Ile Ala His Cys Asn
    50                  55                  60

Leu Glu Pro Leu Val Ser Arg Asp Pro Pro Ala Ser Ala Ser Leu Phe
65                  70                  75                  80

Gln Asp Thr Cys Ala Gly Cys Ala Ser Leu Leu His Gly
                85                  90

<210> SEQ ID NO 10
<211> LENGTH: 57
<212> TYPE: PRT
<213> ORGANISM: Homo sapiens

<400> SEQUENCE: 10

Leu Pro Ala Ser Thr Leu Ser Arg Leu Ser Asn Arg Leu Leu Leu Arg
1               5                   10                  15

Leu Glu Cys Asn Val Val Ile Ile Ala His Cys Asn Leu Glu Pro Leu
            20                  25                  30

Val Ser Arg Asp Pro Pro Ala Ser Ala Ser Leu Phe Gln Asp Thr Cys
        35                  40                  45

Ala Gly Cys Ala Ser Leu Leu His Gly
    50                  55

<210> SEQ ID NO 11
<211> LENGTH: 53
<212> TYPE: PRT
<213> ORGANISM: Homo sapiens

<400> SEQUENCE: 11

Thr Leu Ser Arg Leu Ser Asn Arg Leu Leu Leu Arg Leu Glu Cys Asn
1               5                   10                  15

Val Val Ile Ile Ala His Cys Asn Leu Glu Pro Leu Val Ser Arg Asp
            20                  25                  30

Pro Pro Ala Ser Ala Ser Leu Phe Gln Asp Thr Cys Ala Gly Cys Ala
        35                  40                  45

Ser Leu Leu His Gly
    50

<210> SEQ ID NO 12
<211> LENGTH: 9
<212> TYPE: PRT
<213> ORGANISM: Homo sapiens

<400> SEQUENCE: 12

Arg Leu Ser Asn Arg Leu Leu Leu Arg
1               5

<210> SEQ ID NO 13
<211> LENGTH: 9
<212> TYPE: PRT
<213> ORGANISM: Artificial Sequence
```

```
<220> FEATURE:
<223> OTHER INFORMATION: Synthetic derivative of SEQ ID NO: 12
<220> FEATURE:
<221> NAME/KEY: MISC_FEATURE
<222> LOCATION: (1)..(1)
<223> OTHER INFORMATION: wherein X is His, Arg or Lys

<400> SEQUENCE: 13

Xaa Leu Ser Asn Arg Leu Leu Leu Arg
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic derivative of SEQ ID NO: 12
<220> FEATURE:
<221> NAME/KEY: MISC_FEATURE
<222> LOCATION: (2)..(2)
<223> OTHER INFORMATION: wherein X is Met Leu, Ile or Val

<400> SEQUENCE: 14

Arg Xaa Ser Asn Arg Leu Leu Leu Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic derivative of SEQ ID NO: 12
<220> FEATURE:
<221> NAME/KEY: MISC_FEATURE
<222> LOCATION: (3)..(3)
<223> OTHER INFORMATION: X is Ala, Ser, Thr, Pro or Gly

<400> SEQUENCE: 15

Arg Leu Xaa Asn Arg Leu Leu Leu Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic derivative of SEQ ID NO: 12
<220> FEATURE:
<221> NAME/KEY: MISC_FEATURE
<222> LOCATION: (4)..(4)
<223> OTHER INFORMATION: X is Asp, Asn, Glu or Gln

<400> SEQUENCE: 16

Arg Leu Ser Xaa Arg Leu Leu Leu Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic derivative of SEQ ID NO: 12
<220> FEATURE:
<221> NAME/KEY: MISC_FEATURE
<222> LOCATION: (5)..(5)
<223> OTHER INFORMATION: X is His, Arg or Lys

<400> SEQUENCE: 17

Arg Leu Ser Asn Xaa Leu Leu Leu Arg
1               5
```

```
<210> SEQ ID NO 18
<211> LENGTH: 9
<212> TYPE: PRT
<213> ORGANISM: Artificial Sequence
<220> FEATURE:
<223> OTHER INFORMATION: Synthetic derivative of SEQ ID NO: 12
<220> FEATURE:
<221> NAME/KEY: MISC_FEATURE
<222> LOCATION: (6)..(6)
<223> OTHER INFORMATION: X is Met Leu, Ile or Val

<400> SEQUENCE: 18

Arg Leu Ser Asn Arg Xaa Leu Leu Arg
1               5

<210> SEQ ID NO 19
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: X is Met Leu, Ile or Val

<400> SEQUENCE: 19

Arg Leu Ser Asn Arg Leu Xaa Leu Arg
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic derivative of SEQ ID NO: 12
<220> FEATURE:
<221> NAME/KEY: MISC_FEATURE
<222> LOCATION: (8)..(8)
<223> OTHER INFORMATION: X is Met Leu, Ile or Val

<400> SEQUENCE: 20

Arg Leu Ser Asn Arg Leu Leu Xaa Arg
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic derivative of SEQ ID NO: 12
<220> FEATURE:
<221> NAME/KEY: MISC_FEATURE
<222> LOCATION: (9)..(9)
<223> OTHER INFORMATION: X is His, Arg or Lys

<400> SEQUENCE: 21

Arg Leu Ser Asn Arg Leu Leu Leu Xaa
1               5

<210> SEQ ID NO 22
<211> LENGTH: 83
<212> TYPE: PRT
<213> ORGANISM: Homo sapiens

<400> SEQUENCE: 22

Leu Pro Ala Gln Glu Gly Ala Pro Thr Val Gln Arg Arg Ala Glu Gly
1               5                   10                  15

Leu Leu Lys Cys His Gln Ser Gly Ser Pro Gly Arg Gly Gly Ala Glu
```

-continued

```
                 20                  25                  30

Ser Glu Arg Gly Leu Pro Ala Ser Thr Leu Ser Arg Leu Ser Asn Arg
             35                  40                  45

Leu Leu Leu Ser Ser Arg Ile His Val Gln Asp Val Gln Val Cys Tyr
         50                  55                  60

Met Gly Lys Tyr Val Pro Trp Gln Phe Ala Ala Ser Ile Asn Pro Leu
65                  70                  75                  80

Pro Arg Tyr

<210> SEQ ID NO 23
<211> LENGTH: 47
<212> TYPE: PRT
<213> ORGANISM: Homo sapiens

<400> SEQUENCE: 23

Leu Pro Ala Ser Thr Leu Ser Arg Leu Ser Asn Arg Leu Leu Leu Ser
1               5                  10                  15

Ser Arg Ile His Val Gln Asp Val Gln Val Cys Tyr Met Gly Lys Tyr
             20                  25                  30

Val Pro Trp Gln Phe Ala Ala Ser Ile Asn Pro Leu Pro Arg Tyr
         35                  40                  45

<210> SEQ ID NO 24
<211> LENGTH: 43
<212> TYPE: PRT
<213> ORGANISM: Homo sapiens

<400> SEQUENCE: 24

Thr Leu Ser Arg Leu Ser Asn Arg Leu Leu Leu Ser Ser Arg Ile His
1               5                  10                  15

Val Gln Asp Val Gln Val Cys Tyr Met Gly Lys Tyr Val Pro Trp Gln
             20                  25                  30

Phe Ala Ala Ser Ile Asn Pro Leu Pro Arg Tyr
         35                  40

<210> SEQ ID NO 25
<211> LENGTH: 9
<212> TYPE: PRT
<213> ORGANISM: Homo sapiens

<400> SEQUENCE: 25

Ser Gln Asn Phe Pro Gly Ser Gln Lys
1               5

<210> SEQ ID NO 26
<211> LENGTH: 24
<212> TYPE: DNA
<213> ORGANISM: homo sapiens

<400> SEQUENCE: 26
ccacccatgg caaattccat ggca                                          24

<210> SEQ ID NO 27
<211> LENGTH: 24
<212> TYPE: DNA
<213> ORGANISM: homo sapiens

<400> SEQUENCE: 27
tctagacggc aggtcaggtc cacc                                          24
```

```
<210> SEQ ID NO 28
<211> LENGTH: 21
<212> TYPE: DNA
<213> ORGANISM: homo sapiens

<400> SEQUENCE: 28
aggaaggggc tcccacagtg c                                              21

<210> SEQ ID NO 29
<211> LENGTH: 17
<212> TYPE: DNA
<213> ORGANISM: homo sapiens

<400> SEQUENCE: 29
agcggcgggc tgaagga                                                   17

<210> SEQ ID NO 30
<211> LENGTH: 20
<212> TYPE: DNA
<213> ORGANISM: homo sapiens

<400> SEQUENCE: 30
agcggcgggc tgaaggactc                                                20

<210> SEQ ID NO 31
<211> LENGTH: 24
<212> TYPE: DNA
<213> ORGANISM: homo sapiens

<400> SEQUENCE: 31
cccaggttag aacggtcagc agaa                                           24

<210> SEQ ID NO 32
<211> LENGTH: 24
<212> TYPE: DNA
<213> ORGANISM: homo sapiens

<400> SEQUENCE: 32
gagggtaggg tggtcattgt gtca                                           24

<210> SEQ ID NO 33
<211> LENGTH: 24
<212> TYPE: DNA
<213> ORGANISM: homo sapiens

<400> SEQUENCE: 33
cagcacaaca ggaacattca gtgg                                           24

<210> SEQ ID NO 34
<211> LENGTH: 24
<212> TYPE: DNA
<213> ORGANISM: homo sapiens

<400> SEQUENCE: 34
gggggatttt attgcggtga aagt                                           24

<210> SEQ ID NO 35
<211> LENGTH: 21
<212> TYPE: DNA
<213> ORGANISM: homo sapiens

<400> SEQUENCE: 35
ccaggaaggg gctcccacag t                                              21
```

```
<210> SEQ ID NO 36
<211> LENGTH: 21
<212> TYPE: DNA
<213> ORGANISM: homo sapiens

<400> SEQUENCE: 36
ctgtcacgtc tcagcaatag a                                              21

<210> SEQ ID NO 37
<211> LENGTH: 25
<212> TYPE: DNA
<213> ORGANISM: homo sapiens

<400> SEQUENCE: 37
aaggactcct caagtgccac caaag                                          25

<210> SEQ ID NO 38
<211> LENGTH: 18
<212> TYPE: DNA
<213> ORGANISM: homo sapiens

<400> SEQUENCE: 38
ggaaggggct cccacagt                                                  18

<210> SEQ ID NO 39
<211> LENGTH: 20
<212> TYPE: DNA
<213> ORGANISM: homo sapiens

<400> SEQUENCE: 39
actcctcaag tgccaccaaa                                                20

<210> SEQ ID NO 40
<211> LENGTH: 22
<212> TYPE: DNA
<213> ORGANISM: homo sapiens

<400> SEQUENCE: 40
ctgcttacct caagagcagt ct                                             22

<210> SEQ ID NO 41
<211> LENGTH: 25
<212> TYPE: DNA
<213> ORGANISM: homo sapiens

<400> SEQUENCE: 41
gcagtctatt gctgagacgt gacag                                          25

<210> SEQ ID NO 42
<211> LENGTH: 9
<212> TYPE: PRT
<213> ORGANISM: Homo sapiens

<400> SEQUENCE: 42

Ala Leu Leu Ala Val Gly Ala Thr Lys
1               5

<210> SEQ ID NO 43
<211> LENGTH: 9
<212> TYPE: PRT
<213> ORGANISM: homo sapiens

<400> SEQUENCE: 43
```

```
Ala Leu Asn Phe Pro Gly Ser Gln Lys
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic derivative sequence based on SEQ ID
      NO: 12
<220> FEATURE:
<221> NAME/KEY: MISC_FEATURE
<222> LOCATION: (2)..(2)
<223> OTHER INFORMATION: X is either leucine or isoleucine
<220> FEATURE:
<221> NAME/KEY: MISC_FEATURE
<222> LOCATION: (6)..(8)
<223> OTHER INFORMATION: X is either leucine or isoleucine

<400> SEQUENCE: 44

Arg Xaa Ser Asn Arg Xaa Xaa Xaa Arg
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic derivative of SEQ ID NO: 12

<400> SEQUENCE: 45

Phe Leu Ser Asn Arg Ile Leu Leu Arg
1               5

<210> SEQ ID NO 46
<211> LENGTH: 9
<212> TYPE: PRT
<213> ORGANISM: Homo sapiens

<400> SEQUENCE: 46

Arg Leu Ser Asn Arg Leu Leu Leu Ser
1               5
```

TAG-1 AND TAG-2 PROTEINS AND USES THEREOF

RELATED APPLICATIONS

This application is a national stage filing of International Application No. PCT/US2004/021168, filed on Jul. 1, 2004, which claims benefit under 35 USC §119(e) to US Provisional Application Ser. No. 60/484,077, filed Jul. 1, 2003, the disclosures of which are incorporated herein by reference in their entirety.

US GOVERNMENT RIGHTS

This invention was made with United States Government support under Grant Nos. CA 90815, CA57653 and F32 CA72166, awarded by National Institutes of Health. The United States Government has certain rights in the invention.

BACKGROUND

The mammalian immune system has evolved a variety of mechanisms to protect the host from cancerous cells. An important component of this response is mediated by cells referred to as T cells. Cytotoxic T lymphocytes (CTL) are specialized T cells that primarily function by recognizing and killing cancerous cells or infected cells, but they can also function by secreting soluble molecules referred to as cytokines that can mediate a variety of effects on the immune system. T helper cells primarily function by recognizing antigen on specialized antigen presenting cells, and in turn secreting cytokines that activate B cells, T cells, and macrophages.

A variety of evidence suggests that immunotherapy designed to stimulate a tumor-specific CTL response would be effective in controlling cancer. For example, it has been shown that human CTL recognize sarcomas (Slovin et al., 1986, J Immunol 137, 3042-3048), renal cell carcinomas (Schendel et al., 1993, J Immunol 151, 4209-4220), colorectal carcinomas (Jacob et al., 1997, Int J Cancer 71, 325-332), ovarian carcinomas (Peoples et al., 1993, Surgery 114, 227-234), pancreatic carcinomas (Peiper et al., 1997, Eur J Immunol 27, 1115-1123), squamous tumors of the head and neck (Yasumura et al., 1993, Cancer Res 53, 1461-1468), and squamous carcinomas of the lung (Slingluff et al., 1994, Cancer Res 54, 2731-2737; Yoshino et al., 1994, Cancer Res 54, 3387-3390). The largest number of reports of human tumor-reactive CTLs, however, has concerned melanomas (Boon et al., 1994, Annu Rev Immunol 12, 337-365). The ability of tumor-specific CTL to mediate tumor regression, in both human (Parmiani et al., 2002, J Natl Cancer Inst 94, 805-818; Weber, 2002, Cancer Invest 20, 208-221) and animal models, suggests that methods directed at increasing CTL activity would likely have a beneficial effect with respect to tumor treatment.

Melanoma, or skin cancer, is a disease that is diagnosed in approximately 54,200 persons per year. Conventional therapy for the disease includes surgery, radiation therapy, and chemotherapy. In spite of these approaches to treatment, approximately 7,600 individuals die in the United States every year due to melanoma. Overall, the 5-year survival rate for the disease is 88%. The survival rate drops, however, in more advanced stages of the disease with only about 50% of Stage III patients, and 20-30% of Stage IV patients surviving past five years. In patients where the melanoma has metastasized to distant sites, the 5-year survival dips to only 12%. Clearly, there is a population of melanoma patients that is in need of better treatment options. More recently, in an attempt to decrease the number of deaths attributed to melanoma, immunotherapy has been added to the arsenal of treatments used against the disease.

In order for CTL to kill or secrete cytokines in response to a cancer cell, the CTL must first recognize the cancer cell (Townsend and Bodmer, 1989). This process involves the interaction of the T cell receptor, located on the surface of the CTL, with what is generically referred to as an MHC-peptide complex which is located on the surface of the cancerous cell. MHC (major histocompatibility-complex)-encoded molecules have been subdivided into two types, and are referred to as class I and class II MHC-encoded molecules. In the human immune system, MHC molecules are referred to as human leukocyte antigens (HLA). Within the MHC complex, located on chromosome six, are three different loci that encode for class I MHC molecules. MHC molecules encoded at these loci are referred to as HLA-A, HLA-B, and HLA-C. The genes that can be encoded at each of these loci are extremely polymorphic, and thus, different individuals within the population express different class I MHC molecules on the surface of their cells. HLA-A1, HLA-A2, HLA-A3, HLA-B7; and HLA-B8 are examples of different class I MHC molecules that can be expressed from these loci. The present disclosure involves peptides that are associated with the HLA-A3 molecule.

The peptides which associate with the MHC molecules can either be derived from proteins made within the cell, in which case they typically associate with class I MHC molecules (Rock and Goldberg, 1999, Annu Rev Immunol 17, 739-779); or they can be derived from proteins which are acquired from outside of the cell, in which case they typically associate with class II MHC molecules (Watts, 1997, Annu Rev Immunol 15, 821-850). The peptides that evoke a cancer-specific CTL response most typically associate with class I MHC molecules. The peptides themselves are typically nine amino acids in length, but can vary from a minimum length of eight amino acids to a maximum of twelve amino acids in length. Tumor antigens may also bind to class II MHC molecules on antigen presenting cells and provoke a T helper cell response. The peptides that bind to class II MHC molecules are generally twelve to nineteen amino acids in length, but can be as short as ten amino acids and as long as thirty amino acids.

The process by which intact proteins are degraded into peptides is referred to as antigen processing. Two major pathways of antigen processing occur within cells (Rock and Goldberg, 1999, Annu Rev Immunol 17, 739-779). One pathway, which is largely restricted to cells that are antigen presenting cells such as dendritic cells, macrophages, and B cells, degrades proteins that are typically phagocytosed or endocytosed into the cell. Peptides derived in this pathway typically bind to class II MHC molecules. A second pathway of antigen processing is present in essentially all cells of the body. This second pathway primarily degrades proteins that are made within the cells, and the peptides derived from this pathway primarily bind to class I MHC molecules. Antigen processing by this latter pathway involves polypeptide synthesis and proteolysis in the cytoplasm, followed by transport of peptides to the plasma membrane for presentation. These peptides, initially being transported into the endoplasmic reticulum of the cell, become associated with newly synthesized class I MHC molecules and the resulting complexes are then transported to the cell surface. Peptides derived from membrane and secreted proteins have also been identified. In some cases these peptides correspond to the signal sequence of the proteins which is cleaved from the protein by the signal peptidase. In other cases, it is thought that some fraction of the membrane and secreted proteins are transported from the endoplasmic reticulum into the cytoplasm where processing subsequently occurs.

Once bound to the class I MHC molecule, the peptides are recognized by antigen-specific receptors on CTL. Several methods have been developed to identify the peptides recognized by CTL, each method of which relies on the ability of a CTL to recognize and kill only those cells expressing the appropriate class I MHC molecule with the peptide bound to it. Mere expression of the class I MHC molecule is insufficient to trigger the CTL to kill the target cell if the antigenic peptide is not bound to the class I MHC molecule. Such peptides can be derived from a non-self source, such as a pathogen (for example, following the infection of a cell by a bacterium or a virus) or from a self-derived protein within a cell, such as a cancerous cell. The tumor antigens from which the peptides are derived can broadly be categorized as differentiation antigens, cancer/testis antigens, mutated gene products, widely expressed proteins, and viral antigens (Castelli et al., 2000, J Cell Physiol 182, 323-331).

Immunization with melanoma-derived, class I or class II MHC-encoded molecule associated peptides, or with a precursor polypeptide or protein that contains the peptide, or with a gene that encodes a polypeptide or protein containing the peptide, are forms of immunotherapy that can be employed in the treatment of melanoma. This form of immunotherapy requires that immunogens be identified so that they can be formulated into an appropriate vaccine. Although a variety of melanoma-derived antigens have been identified (Castelli et al., 2000, J Cell Physiol 182, 323-331; Rosenberg, 1999, Immunity 10, 281-287; Van den Eynde and van der Bruggen, 1997, Curr Opin Immunol 9, 684-693; Wang and Rosenberg, 1999, Immunol Rev 170, 85-100), not all of these are appropriate for broad-based immunotherapy as the expression of some of them is limited to the tumor derived from a specific patient. Furthermore, the number of MHC molecules from which tumor-derived peptides have been discovered is relatively limited, and largely restricted to HILA-A2. Thus, it would be useful to identify additional peptides that complex with class I MHC molecules other than HLA-A2. Such peptides would be particularly useful in the treatment of melanoma patients that do not express the HLA-A2 molecule.

It is also particularly useful to identify antigenic peptides that are derived from different parent proteins, even if the derived peptides associate with the same class I MHC molecule. Because an active immune response can result in the outgrowth of tumor cells that have lost the expression of a particular precursor protein for a given antigenic peptide, it is advantageous to stimulate an immune response against peptides derived from more than one parent protein, as the chances of the tumor cell losing the expression of both proteins is the multiple of the chances of losing each of the individual proteins.

The present invention relates to genes, proteins, and peptides that may be used in the diagnosis and treatment of cancer, and in one embodiment the treatment of melanoma. More specifically, the invention relates to the isolation and purification of two novel tumor antigens that can be used as tools for the diagnosis, prevention, and treatment of cancer; and to DNA sequences that code the precursor proteins from which the tumor antigens are derived.

SUMMARY OF VARIOUS EMBODIMENTS OF THE INVENTION

The present invention is directed to a newly discovered gene family with multiple isoforms, designated TAG-1 (SEQ ID NO: 1); TAG-2a (SEQ ID NO: 2); TAG-2b (SEQ ID NO: 3); TAG-2c (SEQ ID NO: 4); and TAG-3 (SEQ ID NO: 5), proteins encoded by such nucleic acid sequences, and antibodies generated against said proteins. TAG-1, TAG-2a, TAG-2b, and TAG-2c all code for one or more proteins that can give rise to the antigenic peptide RLSNRLLLR (SEQ ID NO: 12). The RLSNRLLLR (SEQ ID NO: 12) peptide binds to the class I MHC molecule, HLA-A3, and is recognized by melanoma-specific CTL. The genes, proteins, and peptides described herein may be used as diagnostic indicators of the presence of cancer and/or used in therapeutics to treat cancer.

BRIEF DESCRIPTION OF THE DRAWINGS

FIG. 1. The mRNA sequence and deduced protein sequence for each of the TAG genes coding for the RLSNRLLLR (SEQ ID NO: 12) peptide. The three potential nonstandard initiation codons that are in frame with the open reading frame coding the RLSNRLLLR (SEQ ID NO: 12) peptide are underlined. The shaded nucleotide sequence indicates the 3' prime nucleotide of the 5' exon and the 5' prime nucleotide of the 3' exon at each exon/exon splice site.

FIG. 2B is a schematic drawing of the exon organization of the TAG mRNA.

DETAILED DESCRIPTION OF EMBODIMENTS

Definitions

Figure 2A:
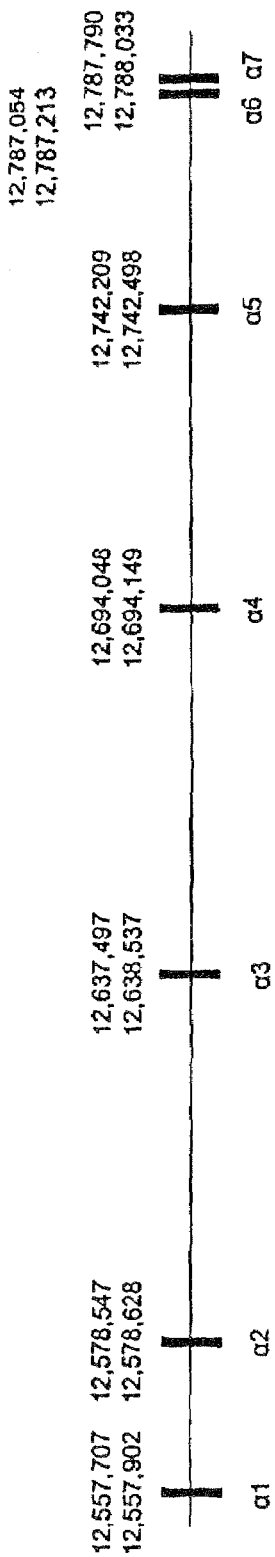
FIGS. 2A & 2B. A schematic drawing of the genomic structure of the TAG gene exons is shown in FIG. 2A. Numbering is according to that obtained in Map Viewer on the NCBI website.

In describing and claiming the invention, the following terminology will be used in accordance with the definitions set forth below.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A polylinker is a nucleic acid sequence that comprises a series of three or more closely spaced restriction endonuclease recognitions sequences.

"Operably linked" refers to a juxtaposition wherein the components are configured so as to perform their usual function. Thus, control sequences or promoters operably linked to a coding sequence are capable of effecting the expression of the coding sequence.

The term "transgene" refers to any polynucleotide which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism. The term "transgenic" refers to any cell which includes a DNA sequence which is inserted by artifice into a cell and becomes part of the genome of the organism which develops from that cell.

As used herein an "exogenous" nucleic acid or amino acid sequence refers to a nucleic acid or protein sequence that has been introduced into a host cell from a point outside the cellular membrane of the cell. Typically the exogenous nucleic acid sequence is a recombinant heterologous gene (i.e. the gene contains a non-native promoter), however the exogenously introduced sequence may also be a gene that is endogenous to the cell.

The term "non-native promoter" as used herein refers to any promoter that has been operably linked to a coding sequence wherein the coding sequence and the promoter are not naturally associated (i.e. a recombinant promoter/coding sequence construct).

"Operably linked" refers to a juxtaposition wherein the components are configured so as to perform their usual function. Thus, control sequences or promoters operably linked to a coding sequence are capable of effecting the expression of the coding sequence.

As used herein, a transgenic cell is any cell that comprises a nucleic acid sequence that has been introduced into the cell in a manner that allows expression of a gene encoded by the introduced nucleic acid sequence.

As used herein, "nucleic acid," "DNA," and similar terms also include nucleic acid analogs, i.e. analogs having other than a phosphodiester backbone. For example, the so called "peptide nucleic acids," which are known in the art and have peptide bonds instead of phosphodiester bonds in the backbone, are considered within the scope of the present invention.

As used herein, the terms "complementary" or "complementarity" are used in reference to polynucleotides (i.e., a sequence of nucleotides) related by the Watson & Crick base-pairing rules, i.e. two nucleic acid sequences that are capable of binding to one another in an anti-parallel base paring arrangement. For example, the sequence 5' A-G-T 3' is complementary to the sequence 3' T-C-A 5'. Complementarity may be "partial," in which some of the nucleic acids' bases are not matched according to the base pairing rules. Or, there may be "complete" or "total" complementarity between the nucleic acids.

As used herein, the term "hybridization" is used in reference to the pairing of complementary nucleic acids. Nucleic acid sequences that share a high degree of complementarity will bind together under high stringent conditions. For example, conditions of high stringency comprise the use of a hybridizing solution containing the nucleic acid sequences in 55% formamide (Gibco-BRL), 10% dextran sulfate, 100 ng/µl salmon sperm DNA in 2XSSC (300 mM NaCl, 30 mM Na citrate, pH 7.0) with a hybridization temperature of 37° C. Washing is then conducted using three changes of 2XSSC at 20° C. for 15 minutes per wash with slight agitation.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) whFerein R is C$_1$-C$_4$ alkyl;

2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or C$_1$-C$_4$ alkyl with the proviso that R and R$_1$ are not both hydrogen;

3. peptides wherein the C terminus is derivatized to —C(O)R$_2$ where R$_2$ is selected from the group consisting of C$_1$-C$_4$ alkoxy, and —NR$_3$R$_4$ where R$_3$ and R$_4$ are independently selected from the group consisting of hydrogen and C$_1$-C$_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and Xaa or X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide structures described herein. The resulting "synthetic peptide" contains amino acids other than the 20 naturally occurring, genetically encoded amino acids at one, two, or more positions of the peptides. For instance, naphthylalanine can be substituted for trytophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" is defined herein as an amino acid exchange within one of the following five groups:

I. Small aliphatic, nonpolar or slightly polar residues: Ala, Ser, Thr, Pro, Gly;

II. Polar, negatively charged residues and their amides: Asp, Asn, Glu, Gin;

III. Polar, positively charged residues: His, Arg, Lys;

IV. Large, aliphatic, nonpolar residues: Met Leu, Ile, Val, Cys

V. Large, aromatic residues: Phe, Tyr, Trp

As used herein, the term "antibody" refers to a polyclonal or monoclonal antibody or a binding fragment thereof such as Fab, F(ab')2 and Fv fragments.

As used herein, the term "TAG polypeptide" refers to an amino acid sequence that comprises a sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 22, SEQ ID NO: 23 and SEQ ID NO: 24.

As used herein, the term "TAG antibody" refers to an antibody that specifically binds to an amino acid sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 22, SEQ ID NO: 23 and SEQ ID NO: 24.

As used herein, the term "biologically active fragments" or "bioactive fragment" of a TAG polypeptide encompasses natural or synthetic portions of the full-length protein that are capable of specific binding to their natural ligand. As used herein, the terms "portion," or "fragment," when used in relation to polypeptides, refer to a continuous sequence of residues, such as amino acid residues, which sequence forms a subset of a larger sequence. Such fragment will necessarily consist of an amino acid sequence that is identical to a sequence present in the larger parent sequence.

As used herein, the term "treating" includes alleviating the symptoms associated with a specific disorder or condition and/or preventing or eliminating said symptoms. For example, treating cancer includes preventing or slowing the growth and/or division of cancer cells as well as killing cancer cells.

EMBODIMENTS

The present invention is directed to a newly discovered gene family, designated TAG (Tumor AntiGen), that encodes multiple isoforms that give rise to cancer antigens. The TAG gene family has at least five family members: TAG-1 (SEQ ID NO: 1); TAG-2a (SEQ ID NO: 2); TAG-2b (SEQ ID NO: 3); TAG-2c (SEQ ID NO: 4); and TAG-3 (SEQ ID NO: 5). Through the usage of non-standard initiation codons, the TAG-1 gene gives rise to three proteins, TAG-1α (SEQ ID NO: 6), TAG-1β (SEQ ID NO: 7), and TAG-2γ (SEQ ID NO: 8). The TAG-2a, TAG-2b, and TAG-2c genes are all predicted to encode the same protein sequence, thus there is only a single TAG-2α, TAG-2β, and TAG-2γ representing the products of the three genes. Accordingly, the TAG-2a, TAG-2b, and TAG-2c members of the gene family give rise to three proteins: TAG-2α (SEQ ID NO: 9), TAG-2β (SEQ ID NO: 10), and TAG-2γ (SEQ ID NO: 11). TAG-1, TAG-2a, TAG-2b, and TAG-2c are characterized herein as genes that give rise to cancer/testis antigens. Furthermore, TAG-1, TAG-2a, TAG-2b, and TAG-2c all code for one or more proteins that can give rise to the antigenic peptide RLSNRLLLR (SEQ ID NO: 12) The RLSNRLLLR (SEQ ID NO: 12) peptide binds to the class I MHC molecule, HLA-A3, and is recognized by melanoma-specific CTL. The TAG-3 member of the gene family also encodes for three proteins (SEQ ID NO: 22, SEQ ID NO: 23 and SEQ ID NO: 24), that while not giving rise to the antigenic peptide RLSNRLLLR (SEQ ID NO: 12), these proteins are expected to generate other cancer/testis antigens.

In accordance with one embodiment of the present invention a purified polypeptide is provided comprising the amino acid sequence of SEQ ID NO: 12. In another embodiment a purified polypeptide is provided comprising the amino acid sequence of SEQ ID NO: 25. In one embodiment the polypeptide comprises the amino acid sequence of SEQ ID NO: 6-11, or an amino acid sequence that differs from any of those sequences by one or more conservative amino acid substitutions. In another embodiment the purified polypeptide comprises an amino acid sequence that differs from SEQ ID NO: 6-11 by less than 5 conservative amino acid substitutions, and in a further embodiment, by 2 or less conservative amino acid substitutions. In one embodiment the present invention is directed to a purified polypeptide that comprises an amino acid selected from the group consisting of XLSNRLLLR (SEQ ID NO: 13), wherein X is His, Arg or Lys;

RXSNRLLLR (SEQ ID NO: 14), wherein X is Met Leu, Ile or Val;

RLXNRLLLR (SEQ ID NO: 15), wherein X is Ala, Ser, Thr, Pro or Gly;

RLSXRLLLR (SEQ ID NO: 16), wherein X is Asp, Asn, Glu or Gln;

RLSNXLLLR (SEQ ID NO: 17), wherein X is His, Arg or Lys;

RLSNRXLLR (SEQ ID NO: 18), wherein X is Met Leu, Ile or Val;

RLSNRLXLR (SEQ ID NO: 19), wherein X is Met Leu, Ile or Val;

RLSNRLLXR (SEQ ID NO: 20), wherein X is Met Leu, Ile or Val; and

RLSNRLLLX (SEQ ID NO: 21), wherein X is His, Arg or Lys.

In accordance with one embodiment of the present invention a purified polypeptide is provided that consists of the amino acid sequence of SEQ ID NO: 6-11, or a bioactive fragment of SEQ ID NO: 6-11, or an amino acid sequence that differs from SEQ ID NO: 6-11 by one to ten conservative amino acid substitutions.

The polypeptides of the present invention may include additional amino acid sequences to assist in the stabilization and/or purification of recombinantly produced polypeptides. These additional sequences may include intra- or inter-cellular targeting peptides or various peptide tags known to those skilled in the art. In one embodiment, the purified polypeptide comprises an amino acid sequence selected from the group consisting of SEQ ID NO: 6-12 and a peptide tag, wherein the peptide tag is linked to the TAG peptide sequence. Suitable expression vectors for expressing such fusion proteins and suitable peptide tags are known to those skilled in the art and commercially available. In one embodiment the tag comprises a His tag.

In another embodiment, the present invention is directed to a purified polypeptide that comprises an amino acid fragment of a TAG polypeptide. More particularly the TAG polypeptide fragment consists of natural or synthetic portions of a full-length polypeptide selected from the group consisting of SEQ ID NO: 6-11 that are capable of specific binding to their natural ligand. Alternatively, the fragment may comprise an antigenic fragment, including fragments of 10-30, 12-19, 8-12 or 9 amino acids in length, of a polypeptide selected from the group consisting of SEQ ID NO: 6-11. In one embodiment the antigenic peptide fragment consists of SEQ ID NO: 12.

The present invention also encompasses nucleic acid sequences that encode the TAG polypeptides. In one embodiment a nucleic acid sequence is provided comprising the sequence of SEQ ID NO: 1, SEQ ID NO: 2, SEQ ID NO: 3, SEQ ID NO: 4, SEQ ID NO: 5 or fragments thereof. All or part of the TAG-1, TAG-2a, TAG-2b, and TAG-2c genes may be used as probes for the detection of the TAG genes in biological samples taken from individuals with cancer or suspected of having cancer. Alternatively, oligonucleotide pairs based on the sequence of the TAG genes may be used as primers for the detection of the TAG genes in biological samples taken from individuals with cancer or suspected of having cancer.

The present invention is also directed to recombinant human TAG gene constructs. In one embodiment, the recombinant gene construct comprises a non-native promoter operably linked to the amino acid coding region of a nucleic acid sequence selected from the group consisting of SEQ ID NO: 1, SEQ ID NO: 3, SEQ ID NO: 4, SEQ ID NO: 5, or fragments thereof. The non-native promoter is preferably a strong constitutive promoter that allows for expression in a predetermined host cell. These recombinant gene constructs can be introduced into host cells to produce transgenic cell lines that synthesize the TAG gene products. Host cells can be selected from a wide variety of eukaryotic and prokaryotic organisms, and two preferred host cells are *E. coli* and yeast cells. In one embodiment the host cell is a human antigen presenting cell.

In accordance with one embodiment, a nucleic acid sequence selected from the group consisting of SEQ ID NO: 1, SEQ ID NO: 3, SEQ ID NO: 4, SEQ ID NO: 5 is inserted into a eukaryotic or prokaryotic expression vector in a manner that operably links the gene sequences to the appropriate regulatory sequences, and a TAG polypeptide is expressed in a eukaryotic or prokaryotic host cell. Suitable eukaryotic host cells and vectors are known to those skilled in the art. The baculovirus system is also suitable for producing transgenic cells and synthesizing the TAG genes of the present invention. One aspect of the present invention is directed to transgenic cell lines that contain recombinant genes that express TAG polypeptides and fragments of the TAG coding sequence. As used herein a transgenic cell is any cell that comprises an exogenously introduced nucleic acid sequence.

In one embodiment the introduced nucleic acid is sufficiently stable in the transgenic cell (i.e. incorporated into the cell's genome, or present in a high copy plasmid) to be passed on to progeny cells. The cells can be propagated in vitro using standard cell culture procedure, or in an alternative embodiment, the host cells are eukaryotic cells and are propagated as part of a plant or an animal, including for example, a transgenic animal. In one embodiment the transgenic cell is a human cell and comprises a nucleic acid sequence selected from the group consisting of SEQ ID NO: 1-5. The present invention also includes non-human transgenic organisms wherein one or more of the cells of the transgenic organism comprise a recombinant gene that expresses a TAG polypeptide.

In accordance with one embodiment a composition is provided for inducing an immune response against the TAG genes, proteins, and peptides described herein. In one embodiment the composition comprises a purified peptide that consists of the amino acid sequence of SEQ ID NO: 12 or SEQ ID NO: 25. In another embodiment the peptide consists of a sequence selected from the group consisting of SEQ ID NO: 6-11, and antigenic fragments of those sequences. Alternatively, the composition for inducing an immune response may comprise a nucleic acid sequence selected from the group consisting of SEQ ID NO: 1, SEQ ID NO: 2, SEQ ID NO: 3, SEQ ID NO: 4, SEQ ID NO: 5. The compositions can be combined with a pharmaceutically acceptable carrier or adjuvant and administered to a mammalian species to induce an immune response. The immune response can take the form of an antibody response, a T helper response, or a CTL response. The immune response may be generated in vitro or in vivo.

In accordance with one embodiment, the TAG proteins or TAG-derived peptides can be used to immunize a non-human recipient such as a mouse, rat, or goat for the production of antibodies that specifically recognize the TAG proteins and peptides. Antibodies to TAG polypeptides may be generated using methods that are well known in the art. In one embodiment, recombinantly produced TAG polypeptides, or fragments thereof are used to generate antibodies against the TAG polypeptides. The recombinantly produced TAG proteins can also be used to obtain crystal structures. Such structures would allow for crystallography analysis that would lead to the design of specific drugs to inhibit TAG function.

In accordance with one embodiment an antibody is provided that binds to a polypeptide selected from the group consisting of SEQ ID NO: 6, SEQ ID NO: 7, SEQ ID NO: 8, SEQ ID NO: 9, SEQ ID NO: 10, and SEQ ID NO: 11. In accordance with one embodiment an antibody is provided that specifically binds to all six TAG polypeptides (i.e. SEQ ID NOs. 6-11). Alternatively, a composition may be provided that comprises one or more antibodies specific for one or two of the individual TAG polypeptides. Alternatively, in one embodiment an antibody is provided that specifically binds to the peptide sequence of SEQ ID NO: 12. In another embodiment an antibody is provided that specifically binds to the peptide sequence of SEQ ID NO: 25. In one embodiment the antibody is a monoclonal antibody. The antibodies may be used with or without modification, and may be labeled by joining them, either covalently or non-covalently, with a reporter molecule. In addition, the antibodies can be formulated with standard carriers and optionally labeled to prepare therapeutic or diagnostic compositions.

Antibodies to TAG polypeptides or peptide fragments thereof may be generated using methods that are well known in the art. For the production of antibodies, various host animals, including rabbits, mice, rats, goats and other mammals, can be immunized by injection with a TAG polypeptide (i.e. TAG-1α, TAG-1β, TAG-1γ, TAG-2α, TAG-2β, and TAG-2γ proteins), or to smaller peptides derived from those proteins. The whole proteins can either be synthesized or the corresponding genes can be inserted in an expression vector and the expressed proteins purified. Methods for expressing genes in expression vectors are well known in the art (Sambrook and Russell, 2001c). Small peptides corresponding to short amino acid sequences within the whole proteins can be synthesized and purified. When small peptides are used as the immunogen, they may be conjugated to carrier proteins such as KLH or tetanus toxoid. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Methods of immunization to achieve a polyclonal antibody response are well known in the art, as are the methods for generating hybridomas and monoclonal antibodies.

For preparation of monoclonal antibodies, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for epitopes of TAG polypeptides together with genes from a human antibody molecule of appropriate biological activity can be used; such antibodies are within the scope of this invention.

According to the invention, techniques described for the production of single chain antibodies (U.S. Pat. No. 4,946,778) can be adapted to produce TAG protein-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for egg surface proteins, derivatives, or analogs. In one embodiment the single chain antibody specifically binds to the amino acid sequence of SEQ ID NO: 12.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab)_2$ fragment, the Fab fragments which can be generated by treating the antibody molecule with papain and a reducing agent, and Fv fragments.

Antibodies generated in accordance with the present invention may include, but are not limited to, polyclonal, monoclonal, chimeric (i.e "humanized" antibodies), single chain (recombinant), Fab fragments, and fragments produced by a Fab expression library. These antibodies can be used as diagnostic agents for the diagnosis of conditions or diseases characterized by expression or overexpression of TAG polypeptides (such as cancer), or in assays to monitor a patients responsiveness to an anti-cancer therapy. In one embodiment antibodies specific for one or more of the TAG polypeptides are used as diagnostics for the detection of the TAG protein in cancer cells.

The antibodies or antibody fragments of the present invention can be combined with a carrier or diluent to form a composition. In one embodiment, the carrier is a pharmaceutically acceptable carrier. Such carriers and diluents include sterile liquids such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose, and related sugar solution, and glycols such as, propylene glycol or polyethylene glycol, are preferred liquid carriers, particularly for injectable solutions.

In accordance with one embodiment the detection of TAG nucleic acid sequences or polypeptides is used as a diagnostic mark for detecting cancer. More particularly, in one embodiment the detection of TAG mRNA or TAG polypeptides or peptides is diagnostic for cancer. In another embodiment the TAG genes, the TAG proteins, or the TAG-derived peptides can be used to immunize an individual to induce an immune response. The induced response may include T helper cells or CTL specific for the TAG-derived peptides. The induced immune response may be useful in preventing the development of cancer in an individual without cancer, and it may be useful in eliminating or preventing the further spread of the disease in an individual with cancer. In one embodiment the TAG genes are placed in an expression vector and expressed in an antigen presenting cell. Alternatively, the TAG proteins or TAG-derived peptides may be added to antigen presenting cells. In either case, the antigen presenting cells will now present TAG-derived peptides which can be used to stimulate an in vitro T helper cell or CTL response. The T helper cells or CTL can then be used as diagnostics to detect the expression of the TAG genes in tumor or other cells. The T helper cells or CTL can also be infused into a cancer patient as a treatment for cancer.

Accordingly, one embodiment of the invention is directed to the use of TAG polypeptides, peptides and nucleic acids as diagnostic markers for neoplastic disease such as cancer. The method comprises the steps of screening for elevated levels or inappropriate expression of TAGs, including the expression of TAGs in somatic tissues. The term "inappropriate expression" includes any non-typical expression that is deleterious to the cell or host organism, including for example, expression in a cell type that normally does not express the gene product, or expression of a modified form of the protein that impacts cell function. Such screens could be conducted using antibodies specific for the TAG polypeptides. Alternatively, antibodies directed against TAG polypeptides can be used in assays to monitor patients being treated with anticancer therapies to monitor the effectiveness of the therapy.

All or part of the TAG-1, TAG-2a, TAG-2b, and TAG-2c genes may be used as probes for the detection and quantification of the corresponding genes in biological samples isolated from an individual with cancer or suspected of having cancer. For example, both Northern hybridization and dot blot hybridization may be used to detect and quantify the TAG genes. Methods for such procedures are well known in the art (Sambrook and Russell, 2001a). Combinations of oligonucleotide pairs based on the sequence of the TAG genes may be used as PCR primers to detect the TAG gene mRNA in biological samples by using the reverse transcriptase polymerase chain reaction (RT-PCR). Specific primer pairs are illustrated in the Examples below, but other pairs can easily be identified by those schooled in the art. Methods for RT-PCR are well known in the art (Sambrook and Russell, 2001b). Because the TAG genes have been shown to be expressed only in cancerous tissue, placenta, and testis, their detection in biological samples other than placenta and testis would indicate the presence of cancer in an individual for which a diagnosis had not yet been made. Alterations in the level of mRNA relative to a control RNA sample would be useful in monitoring the prognosis of the disease in an individual known to have cancer, and in monitoring the results of immunotherapy directed against cancer cells expressing the TAG genes.

The tumor antigens of the present invention encompass the proteins that can be expressed from the TAG-1, TAG-2a, TAG-2b, and TAG-2c genes. These proteins include TAG-1α, TAG-1β, TAG-1γ, TAG-2α, TAG-2β, and TAG-2γ. In accordance with one embodiment the tumor antigens of the present invention encompass small peptides, typically nine amino acids in length, but generally no less than eight and no more than twenty amino acids in length, that are derived from the TAG-1α, TAG-1β, TAG-1γ, TAG-2α, TAG-2β, and TAG-2γ proteins. Further, because it has been shown that antigens can be derived by the non-traditional translation of genes (Mayrand and Green, 1998; Shastri et al., 2002), the tumor antigens of the present invention encompass any peptide that can be expressed from the TAG-1, TAG-2a, TAG-2b, and TAG-2c genes, whether by traditional or non-traditional translation.

The TAG-1, TAG-2a, TAG-2b, and TAG-2c genes are known to be expressed in melanoma, myelogenous leukemia, lung cancer, breast cancer, ovarian cancer, colon cancer, gastric cancer, and prostate cancer and thus may be used as immunogens to prevent, eliminate, or delay the progression of those cancers. These same genes may also be expressed in untested forms of cancer and thus may be useful in their ability to prevent, eliminate or delay the progression of additional cancers.

Antibodies generated with specificity for the TAG-1α, TAG-1β, TAG-1γ, TAG-2α, TAG-2β, and TAG-2γ proteins are used in accordance with one embodiment to detect the corresponding proteins in biological samples. Tire biological sample could come from an individual whom is suspected of having cancer and thus detection would serve to diagnose the cancer. Alternatively, the biological sample may come from an individual known to have cancer, and detection of the TAG proteins would serve as an indicator of disease prognosis or treatment efficacy. Appropriate immunoassays are well known in the art and include, but are not limited to, immunohistochemistry, flow cytometry, radioimmunoassay, western blotting, and ELISA. Biological samples suitable for such testing would include, but are not limited to, cells, tissue biopsy specimens, whole blood, plasma, serum, sputum, cerebrospinal fluid, pleural fluid, and urine.

Antigens recognized by T cells, whether helper T lymphocytes or CTL, are not recognized as intact proteins, but rather as small peptides that associate with class I or class II MHC proteins on the surface of cells. During the course of a naturally occurring immune response antigens that are recognized in association with class II MHC molecules on antigen presenting cells are acquired from outside the cell, internalized, and processed into small peptides that associate with the class II MHC molecules. Conversely, the antigens that give rise to proteins that are recognized in association with class I MHC molecules are generally proteins made within the cells, and these antigens are processed and associate with class I MHC molecules. It is now well known that the peptides that associate with a given class I or class II MHC molecule are characterized as having a common binding motif, and the binding motifs for a large number of different class I and II MHC molecules have been determined. It is also well known that synthetic peptides can be made which correspond to the sequence of a given antigen and which contain the binding motif for a given class I or II MHC molecule. These peptides can then be added to appropriate antigen presenting cells, either in vitro or in vivo, and be used to stimulate a T helper cell or CTL response. The binding motifs, methods for synthesizing the peptides, and methods for stimulating a T helper cell or CTL response are all well known and readily available.

Thus, antigens of this invention may take several forms. The TAG-1, TAG-2a, TAG-2b, and TAG-2c genes may be used alone, in combination with one another, or in combination with the genes for other antigens. The genes would be cloned into a vector and operationally linked to a promoter. Vectors may be chosen such that the genes would be expressed in bacteria or insect cells with the purpose of purifying the TAG-1α, TAG-1β, TAG-1γ, TAG-2α, TAG-2β, and TAG-2γ proteins. The vector may be a mammalian expression vector system with the recipient cells being dendritic cells or cultured mammalian cell lines. Transient or stable transfection of these cells with the gene of interest would provide cells which can then be used either in vitro or in vivo to stimulate a T helper cell or CTL immune response to the antigens of this invention. Alternatively, the vector may include all or part of a viral or bacterial genome, for example vaccinia virus, fowlpox virus, adenovirus, or BCG. Dendritic cells or cultured mammalian cell lines can be infected in vitro to provide antigenic cells for the stimulation of T helper cell or CTL responses. The viral or bacterial vectors expressing the genes of interest could also be used to immunize an individual with the intent of stimulating an immune response to the antigens of this invention. The vectors, methods of cloning, and methods of stimulating an immune response to the expressed genes are all well known in the art.

The antigens of this invention may also take the form of the whole proteins TAG-1α, TAG-1β, TAG-1γ, TAG-2α, TAG-2β, and TAG-2γ. The whole proteins may be added to autologous dendritic cells and used to stimulate a T helper cell or CTL response in vitro. The in vitro generated T helper cells or CTL can then be infused into a patient with cancer (Yee et al., 2002), and specifically a patient with a form of cancer that expresses one or more of the TAG-1, TAG-2a, TAG-2b, and TAG-2c genes. The TAG-1α, TAG-1β, TAG-1γ, TAG-2α, TAG-2β, and TAG-2γ proteins may also be used to vaccinate an individual. The proteins may be injected alone, but most often they would be administered in combination with an adjuvant. The proteins may also be added to dendritic cells in vitro, with the dendritic cells being subsequently transferred into an individual with cancer with the intent of stimulating an immune response.

The antigens of this invention may also take the form of small peptides. Peptides that bind to class I MHC molecules and that stimulate a CTL response are commonly nine amino acids in length, but may be as short as eight amino acids in length, and as long as fourteen amino acids in length. The peptides which bind to a particular class I MHC molecule share a common binding motif in which particular amino acid residues within the sequence generally have a very restricted allowable number of amino acids which can occupy that position, while amino acids at the remaining positions are largely without restriction. Due to the nature of the peptide binding site on class II MHC molecules, class II MHC binding peptides can be as short as ten amino acids, and may be as long as thirty amino acids in length. Like class I MHC binding peptides, class II MHC binding peptides have binding motifs for particular class II MHC molecules. Because of the extended nature of the class II MHC binding peptides relative to class I MHC binding peptides, a class II antigenic peptide may encompass many overlapping sequences with a common core sequence. An extensive literature exists describing the motifs of the peptides that bind to the various class I and class II MHC molecules.

Prior to identifying the TAG-1, TAG-2a, TAG-2b, and TAG-2c gene sequences, the RLSNRLLLR peptide (SEQ ID NO: 12) was identified as an HLA-A3 binding peptide that was recognized by melanoma reactive CTL. This peptide is derived from proteins expressed from the antigenic genes of this invention, but as described in the Examples, had to be identified independent of any knowledge of the gene or proteins from which it was derived. Now that the TAG-1, TAG-2a, TAG-2b, and TAG-2c gene sequences have been identified, it is possible to predict many of the antigenic peptides from the coded proteins. Predicted peptide antigens can be synthesized and readily tested in vitro for their ability to stimulate a T helper cell or CTL response. The binding motifs, methods of peptide synthesis, and methods of in vitro stimulation and testing are all well known and readily available to the skilled practitioner.

It is also well-known in the art that the naturally occurring sequence of the antigenic peptides is not always optimal for stimulating an immune response. Peptide analogs can readily be synthesized that retain their ability to stimulate a particular immune response, but which also gain several beneficial features which include, but are not limited to the following: (i) Substitutions may be made in the peptide at residues known to interact with the MHC molecule. Such substitutions can have the effect of increasing the binding affinity of the peptide for the MHC molecule and can also increase the lifespan of the peptide-MHC complex, the consequence of which is that the analog is a more potent stimulator of an immune response than is the original peptide. (ii) The substitutions may be at positions in the peptide that interact with the receptor on the T helper cells or CTL, and have the effect of increasing the affinity of interaction such that a stronger immune response is generated. (iii) Additionally, the substitutions may have no effect on the immunogenicity of the peptide per se, but rather than may prolong its biological half life or prevent it from undergoing spontaneous substitutions or alternations which might otherwise negatively impact on the immunogenicty of the peptide.

The antigens of this invention can also be used as a vaccine for cancer, and more specifically for melanoma and myelogenous leukemia. As described above, the antigens may take the form of genes, proteins, or peptides. The vaccine may include only the antigens of this invention or they may include other cancer antigens that have been identified. Pharmaceutical carriers, diluents and excipients are generally added that are compatible with the active ingredients and acceptable for pharmaceutical use. Examples of such carriers include, but are not limited to, water, saline solutions, dextrose, or glyercol. Combinations of carriers may also be used. The vaccine compositions may further incorporate additional substances to stabilize pH, or to function as adjuvants, wetting agents, or emulsifying agents, which can serve to improve the effectiveness of the vaccine.

The composition may be administered parenterally or orally, and, if perenterally, either systemically or topically. Parenteral routes include subcutaneous, intravenous, intradermal, intramuscular, intraperitoneal, intranasal, transdermal, or buccal routes. One or more such routes may be employed. Parenteral administration can be, for example, by bolus injection or by gradual perfusion over time. Alternatively, or concurrently, administration may be by the oral route.

It is understood that the suitable dosage of an immunogen of the present invention will depend upon the age, sex, health, and weight of the recipient, the kind of concurrent treatment, if any, the frequency of treatment, and the nature of the effect desired, however, the most preferred dosage can be tailored to the individual subject, as determined by the researcher or clinician. The total dose required for any given treatment will commonly be determined with respect to a standard reference dose based on the experience of the researcher or clinician, such dose being administered either in a single treatment or in a series of doses, the success of which will depend on the production of a desired immunological result (i.e., successful production of a T helper cell and/or CTL-mediated response to the antigen, which response gives rise to the prevention and/or treatment desired). Thus, the overall administration schedule must be considered in determining the success of a course of treatment and not whether a single dose, given in isolation, would or would not produce the desired immunologically therapeutic result or effect. Thus, the therapeutically effective amount (i.e., that producing the desired T helper cell and/or CTL-mediated response) will depend on the antigenic composition of the vaccine used, the nature of the disease condition, the severity of the disease condition, the extent of any need to prevent such a condition where it has not already been detected, the manner of administration dictated by the situation requiring such administration, the weight and state of health of the individual receiving such administration, and the sound judgment of the clinician or researcher. Needless to say, the efficacy of administering additional doses, and of increasing or decreasing the interval, may be re-evaluated on a continuing basis, in view of the recipent's immunocompetence (for example, the level of T helper cell and/or CTL activity with respect to tumor-associated or tumor-specific antigens).

The concentration of the T helper or CTL stimulatory peptides or proteins of the invention in pharmaceutical formulations are subject to wide variation, including anywhere from less than 0.01% by weight to as much as 50% or more. Factors such as volume and viscosity of the resulting composition should also be considered. The solvents, or diluents, used for such compositions include water, possibly PBS (phosphate buffered saline), or saline itself, or other possible carriers or excipients. The immunogens of the present invention may also be contained in artificially created structures such as liposomes, which structures may or may not contain additional molecules, such as proteins or polysaccharides, inserted in the outer membranes of said structures and having the effect of targeting the liposomes to particular areas of the body, or to particular cells within a given organ or tissue. Such targeting molecules may commonly be some type of immunoglobulin. Antibodies may work particularly well for targeting the liposomes to tumor cells.

The present invention is also directed to a vaccine in which a peptide or polypeptide or active fragment of the present invention is delivered or administered in the form of a polynucleotide coding the peptide or polypeptide or active fragment, whereby the peptide or polypeptide or active fragment is produced in vivo. The polynucleotide may be included in a suitable expression vector and combined with a pharmaceutically acceptable carrier.

The vaccine compositions may be used prophylactically for the purposes of preventing cancer in an individual that does not currently have cancer, or they may be used to treat an individual that already has cancer. Prevention relates to a process of prophylaxis in which the individual is immunized prior to the induction or onset of cancer. For example, individuals with a history of severe sunburn and at risk for developing melanoma, might be immunized prior to the onset of the disease. Alternatively, individuals that already have cancer can be immunized with the antigens of the present invention so as to stimulate an immune response that would be reactive against the cancer. A clinically relevant immune response would be one in which the cancer is completely regresses and is eliminated from the patient, and it would also include those responses in which the progression of the cancer is blocked without being eliminated.

In one embodiment, the present invention provides methods of screening for agents, small molecules, or proteins that interact with polypeptides comprising a sequence selected from the group consisting of SEQ ID NO: 6-11 or bioactive fragments thereof. The invention encompasses both in vivo and in vitro assays to screen small molecules, compounds, recombinant proteins, peptides, nucleic acids, antibodies etc. which bind to or modulate the activity of TAG polypeptide and are thus useful as therapeutic or diagnostic markers for cancer. As used herein, modulating the activity of a TAG polypeptide includes interfering or altering the TAG polypeptides ligand binding properties.

Example 1

Isolation of the TAG Genes

Cell Lines

The melanoma lines A375, AVL3-Mel, DM6, DM13, DM14, DM93, DM122, DM281, DM319, DM331, DM472, EB81-Mel, HT144, LB373-Mel, Na8-Mel, SK-MelL-2, SK-Mel-5, SK-Mel-28, VMM1, VMM5, VMM12, VMM15, VMM17, VMM18, VMM19, VMM34, VMM39, VMM39, VMM64, VMM86, VMM105, VMM150, VMM273, and VMM330 were maintained in RPM11640 supplemented with 5-10% FBS and 2 mM L-glutamine. K562, a myelogenous leukemia (Lozzio and Lozzio, 1979 Leuk Res 3, 363-370), and the B-lymphoblastoid cell lines JY, VMM12-EBV, and VMM18-EBV were maintained in the same media. C1R-A3 and T2-A3, were maintained in the same media supplemented with 200 µg/ml G418.

The lung tumor lines SK-Mes-1, SK-LU-1, Calu-1, VLU-6, VLU-19, VBT-2, and TTB-250; the breast tumor lines MCF-7 (KR), MDA-MB-468, MDA-MB-453, TTB-173, VA-B5A, SK-BR-3, BRC-751, and BRC-173; ovarian tumor lines CA-OV-14, SK-OV-3, TTB-6, and VAO-12; colon tumor lines CCL-228, CL-188, HT-29, VCR-8, SW-48, and VCR-4; brain tumor lines CRL-1690, HTB-12, HTB-14, and HTB-17; prostate tumor lines Du145, LnCap, and PC-3; pharyngeal squamous cell carcinoma FaDu; tongue squamous cell carcinoma SCC4; and cervical cell carcinoma SIHA were also used and cultured in the same manner as the melanoma tumor cell lines. Four cryopreserved prostate carcinoma clinical isolates were also obtained from the Tissue Procurement Facility at the University of Virginia. cDNA from a prostate carcinoma was purchased from Biochain.

CTL Line

VMM18-specific CTL have been described previously (Skipper et al., 1996, J Immunol 157, 5027-5033). CTL were expanded in bulk culture using anti-CD3 antibody (Greenberg and Cheever, 1985, Surv Immunol Res 4, 283-296) and cryopreserved in aliquots of 1-5×10⁷ cells for use in epitope reconstitution assays.

Isolation of HLA-A3 Associated Peptides

Immunoaffinity purification of class I MHC molecules from aliquots of $6-8\times10^{10}$ VMM18 tumor cells was performed as described (Hogan et al., 1998, Cancer Res 58, 5144-5150), except that the HLA-A3-specific monoclonal antibody GAP-A3, bound to protein A-Sepharose, was used to isolate the HLA-A3 molecules.

Peptide Fractionation

Peptide extracts were fractionated by RP-HPLC using an Applied Biosystems model 140B system. The extracts were concentrated by vacuum centrifugation and injected onto a Higgins (Mountain View, Calif.) C18 HAISIL column (2.1 mm×4 cm, 300 Å, 5 µm). The peptides were eluted with a gradient of acetonitrile/0.085% trifluoroacetic acid (TFA)* in 0.1% TFA/water, with the concentration of acetonitrile increasing from 0 to 9% (0 to 5 min), 9 to 36% (5 to 55 min), and 36 to 60% (55 to 62 min). Second dimension fractionations of selected first dimension (TFA) fractions were accomplished using the same gradient but with the substitution of heptafluorobutyric acid (HFBA) for TFA. A third dimension of RP-HPLC was achieved using an Eldex (Napa, Calif.) MicroPro pump, a homemade C18 microcapillary column and an Applied Biosystems model 785A UV absorbance detector. The column was made by packing a 27-cm bed of 10-µm C18 particles in a section of 285 µm o.d.×75 µm i.d. fused silica. Peptides in a selected second dimension fraction were loaded onto this column and eluted with a gradient of acetonitrile/0.67% triethylamine acetate (TEAA)/water in 0.1% triethylamine acetate/water, with the concentration of acetonitrile increasing from 0 to 60% in 40 min. The flow rate was approximately 300 nl/min, and fractions were collected into 25 µl of 0.1% acetic acid every 30 seconds. In all RP-HPLC experiments, peptides were detected by monitoring UV absorbance at 214 nm.

CTL Epitope Reconstitution Assay

Aliquots of each RP-HPLC fraction were tested for the presence of peptides that could sensitize C1R-A3 targets for lysis by VMM18 CTL in standard four-hour 51Cr-release assays as previously described (Hogan et al., 1998, Cancer Res 58, 5144-5150).

Mass Spectrometric Analyses

Active RP-HPLC fractions were screened by on-line RP-HPLC/electrospray ionization mass spectrometry (MS) using a homemade microcapillary column and a Finnigan-MAT TSQ 7000 triple quadrupole mass spectrometer (Finnigan, San Jose, Calif.). Approximately one percent of the active RP-HPLC fraction was loaded onto a section of 185-µm o.d.×75-µm i.d. fused silica packed with 10 to 12 cm of 10 µm C18 particles. Peptides were eluted directly into the mass spectrometer using a 10-minute 0-60% acetonitrile in 0.1 M acetic acid gradient. Ions were formed by electrospray ionization, and mass spectra were recorded by scanning between mass to charge ratios (m/z) 300 and 1400 every 1.5 seconds.

Active second dimension HPLC fractions were analyzed using an effluent splitter on the microcapillary HPLC column. The column (360-µm o.d.×100-µm i.d. with a 25-cm C18 bed) was connected with a zero dead volume tee (Valco, Houston, Tex.) to two pieces of fused silica of different lengths (25-µm and 40-µm i.d.). Peptides were eluted with a 34-minute gradient of 0-60% acetonitrile in 0.1 M acetic acid. The 25-µm capillary deposited one-fifth of the HPLC effluent into the wells of a microtiter plate for use in a CTL epitope reconstitution assay, while the remaining four-fifths of the effluent was directed into the mass spectrometer, with mass spectra recorded as described above.

Peptide sequences were determined by collision-activated dissociation (CAD) tandem mass spectrometry using an LCQ (Finnigan) ion trap mass spectrometer and methods as described (Cox et al., 1994, Science 264, 716-719).

Peptide Synthesis

Peptides were synthesized using a Gilson (Madison, Wis.) AMS 422 multiple peptide synthesizer using conventional FMOC chemistry. Peptides were purified by RP-HPLC using a 4.6-mm i.d.×100-mm long POROS (Perseptive Biosystems, Cambridge, Mass.) column and a 10-minute 0 to 60% acetonitrile in 0.1% TFA gradient.

Total mRNA Isolation

Total RNA was prepared from $2-10\times10^6$ cells using the RNeasy® Mini kit (Qiagen, Valencia, Calif.) as per the kit instructions. RNA was quantified by absorbance at 260 nm.

PCR Primers

The gene specific primers (GSP) 1361 and 1362 are specific for GAPDH and the remaining primers are directed towards the TAG gene.

| 1361: | 5'-CCACCCATGGCAAATTCC ATGGCA-3' | (SEQ ID NO: 26) |
|---|---|---|
| 1362: | 5'-TCTAGACGGCAGGTCAGG TCCACC-3' | (SEQ ID NO: 27) |
| A52: | 5'-AGGAAGGGGCTCCCACAG TGC-3' | (SEQ ID NO: 28) |

-continued

| A73: | 5'-AGCGGCGGGCTGAAGGA-3' | (SEQ ID NO: 29) |
| --- | --- | --- |
| A73.92: | 5'-AGCGGCGGGCTGAAGGACTC-3' | (SEQ ID NO: 30) |
| C723: | 5'-CCCAGGTTAGAACGGTCAGCAGAA-3' | (SEQ ID NO: 31) |
| E600: | 5'-GAGGGTAGGGTGGTCATTGTGTCA-3' | (SEQ ID NO: 32) |
| F473: | 5'-CAGCACAACAGGAACATTCAGTGG-3' | (SEQ ID NO: 33) |
| G608: | 5'-GGGGGATTTTATTGCGGTGAAAGT-3' | (SEQ ID NO: 34) |
| RLS-F-A: | 5'-CCAGGAAGGGGCTCCCACAGT-3' | (SEQ ID NO: 35) |
| RLS-F-B: | 5'-CTGTCACGTCTCAGCAATAGA-3' | (SEQ ID NO: 36) |
| RLS-F-15: | 5'-AAGGACTCCTCAAGTGCCACCAAAG-3' | (SEQ ID NO: 37) |
| RLS-F-180: | 5'-GGAAGGGGCTCCCACAGT-3' | (SEQ ID NO: 38) |
| RLS-F-216: | 5'-ACTCCTCAAGTGCCACCAAA-3' | (SEQ ID NO: 39) |
| RLS-R-331: | 5'-CTGCTTACCTCAAGAGCAGTCT-3' | (SEQ ID NO: 40) |
| RLS-R-119: | 5'-GCAGTCTATTGCTGAGACGTGACAG-3' | (SEQ ID NO: 41) |

RT-PCR

RT-PCR (Promega, Madison, Wis.) was used to screen VMM12 and VMM18 mRNA for the expression of a gene coding the RLSNRLLLR sequence. The primer pairs RLS-F-180/RLS-R-331 and RLS-F-216/RLS-R-331 were used to amplify 152 bp and 116 bp fragments, respectively. RT-PCR conditions were: 48° C. for 45 min; 94° C. for 2 min; 35 cycles of 94° C. for 30 s, 50° C. for 60 s, 68° C. for 60 s; 68° C. for 5 min. For all other PCR reactions, total RNA was first converted to cDNA by using the SuperScript™ First-Strand Synthesis System (Invitrogen, Carlsbad, Calif.). PCR was then performed on 250 ng of cDNA using Platinum Taq High Fidelity (Invitrogen). The PCR mixes were heated to 94° C. for 2 min, 30 cycles of amplification were performed, followed by a final extension at 68° C. for 5 min. When amplifying the TAG genes, the 30 cycles consisted of 94° C. for 30 s, 62° C. for 30 s, and 68° C. for 60 s. When the GAPDH gene was amplified, the 30 cycles consisted of 94° C. for 30 s, 60° C. for 30 s, and 68° C. for 60 s. The PCR products were visualized on ethidium bromide stained agarose gels.

DNA Sequencing

Automated DNA sequencing was performed at the University of Virginia DNA Sequencing Core on either an Applied Biosystems 377 Prism DNA Sequencer or 3100 Genetic Analyzer, using Big Dye terminator chemistry with Taq DNA polymerase.

Rapid Identification of cDNA Ends (RACE)

The GeneRacer™ system (Invitrogen) was used to perform both 5' and 3' RACE. For the 5' RACE procedure, the GeneRacer™ 5' Primer was used in conjunction with the GSP RLS-R-119 (5'-GCAGTCTATTGCTGAGACGTGACAG-3'; SEQ ID NO: 41). Cycling conditions were: 94° C. for 2 min; 5 cycles of 94° C. for 30 s, 76° C. for 2 min; 5 cycles of 94° C. for 30 s, 74° C. for 2 min; 5 cycles of 94° C. for 30 s, 72° C. for 2 min; 15 cycles of 94° C. for 30 s, 70° C. for 30s, 72° C. for 2 min; 72° C. for 5 min).

Nested PCR was used for the 3' RACE procedure. Outside reactions used the GeneRacer™ 3' primer in conjunction with either of the GSP primers RLS-F-A or RLS-F-15. Cycling conditions for the RLS-F-A PCR consisted of 94° C. for 2 min; 5 cycles of 94° C. for 30 s, 68° C. for 2 min; 5 cycles of 94° C. for 30 s, 66° C. for 2 min; 20 cycles of 94° C. for 30 s, 61° C. for 30 s, 68° C. for 2 min; 68° C. for 10 min. Cycling conditions for the RLS-F-15 PCR consisted of 94° C. for 2 min; 5 cycles of 94° C. for 30 s, 72° C. for 2 min; 5 cycles of 94° C. for 30 s, 70° C. for 2 min; 20 cycles of 94° C. for 30 s, 65° C. for 30 s, 68° C. for 2 min; 68° C. for 10 min. Inside reactions used the 3' GeneRacer™ nested primer with the GSP primer RLS-F-B. Cycling conditions were: 94° C. for 2 min; 14 cycles of 94° C. for 30 sec, 76° C. (decreasing 0.5° C. per cycle) for 2 min; 16 cycles of 94° C. for 30 s, 68° C. (decreasing 0.5° C. per cycle) for 30 s, 68° C. for 2 min; 68° C. for 10 min.

The PCR products were visualized on ethidium bromide stained low melting agarose gels, and selected bands were purified using the QIAquick® (Qiagen) purification system. The purified DNA was cloned into pCR4TOPO® (Invitrogen), transformed into One Shot® TOP10 Chemically Competent E. coli (Invitrogen), and selected with 100 µg/ml ampicillin on LB agar. DNA from individual colonies was purified using the Qiagen Plasmid Mini Kit.

VMM18 CTL Recognize Three Distinct HLA-A3-Restricted Epitopes

The peptides bound to HLA-A3 molecules on $8 \times 10^{10}$ VMM18 tumor cells were purified as described in Materials and Methods, and fractionated by RP-HPLC using TFA as the organic modifier. A CTL epitope reconstitution assay was performed using 2.5% of each RP-HPLC fraction ($2 \times 10^9$ cell equivalents), and three peaks of activity were observed. Peak B activity (fractions 26-28) corresponds to the previously described ALLAVGATK (SEQ ID NO: 42) peptide from Pmel17/gp100.

Identification of the Antigenic Peptides

Pooled active fractions 15-17 (peak A), and active fraction 38 (peak C) were each further fractionated by RP-HPLC using HFBA as the organic modifier. In CTL epitope reconstitution assays, fractions 26 and 27 of this second fractionation of peak A contained the active peptide, and fractions 66 and 67 of a second fractionation of peak C contained the active peptide. The peptides were further fractionated by a third round of RP-HPLC, using TEAA as the organic modifier. In CTL epitope reconstitution assays, the peak A antigenic peptide was found to elute in fractions 22-24, while the peak C antigenic peptide was present primarily in fractions 32-34.

The Active Peptide in Peak A is SQNFPGSQK (SEQ ID NO: 25)

Mass spectrometric analysis of the active third dimension RP-HPLC fractions representing peak A indicated that the abundance of the m/z 497 ion strongly correlated with the CTL epitope reconstituting activity. Analysis of fragment masses obtained from the CAD mass spectrum allowed the determination of the peptide sequence as SQNFPGSQK (SEQ ID NO: 25). This synthetic peptide was active in sensitizing C1R-A3 targets for lysis by VMM18 CTL at concentrations as low as 10 pM (FIG. 1). It was subsequently determined by RP-HPLC and mass spectrometry that the synthetic peptide SQNFPGSQK (SEQ ID NO: 25) co-eluted with the unknown m/z 497 in the active second and third dimension fractions (data not shown), indicating that this sequence represents the naturally processed and presented epitope.

The Active Peptide in Peak C is RLSNRLLLR (SEQ ID NO: 12)

Figure 2B:
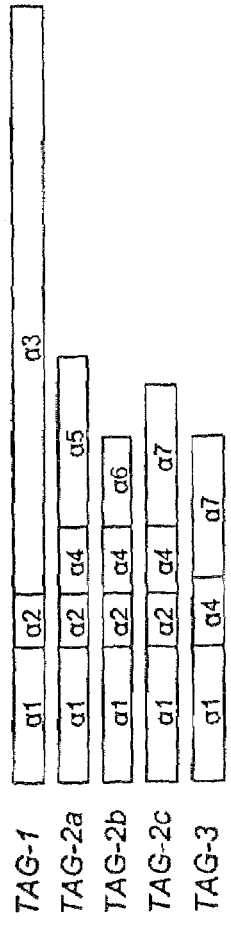

Analysis of the active third dimension peak C fractions showed that the biological activity in epitope reconstitution assays correlated with the abundance of the m/z 571 ion. Analysis of the CAD mass spectra suggested that the peptide sequence included four leucine or isoleucine residues (labeled as X because these residues are not distinguishable by low-energy CAD). A mixture of peptides was therefore synthesized, with leucine and isoleucine incorporated at each of four positions in the sequence RXSNRXXXR (SEQ ID NO: 44), and this peptide cocktail of 16 peptides had potent epitope reconstituting activity (FIG. 2A). Each of the sixteen peptides was individually synthesized and tested in epitope reconstitution assays. A range of activities was observed, with most of the sequences sensitizing C1R-A3 targets for at least some VMM18 CTL-specific lysis, and with no one sequence being significantly and reproducibly superior to all of the others (data not shown). Subsequent RP-HPLC co-elution studies clearly demonstrated, however, that the unknown m/z 571 in the active fractions was RLSNRLLLR (SEQ ID NO: 12), and the epitope reconstitution assay showed that this peptide is active at concentrations as low as 10 pM (FIG. 2B).

Both SQNFPGSQK (SEQ ID NO: 25) and RLSNRLLLR (SEQ ID NO: 12) are Presented on at Least One Other HLA-A3+ Melanoma Mass spectrometric analysis of RP-HPLC fractionated peptides eluted from immunoaffinity purified HLA-A3 from the melanoma cell line VMM12 demonstrated that SQNFPGSQK (SEQ ID NO: 25) and RLSNRLLLR (SEQ ID NO: 12) peptides were both present in the expected fractions (data not shown) and thus, both peptides represent novel shared melanoma antigens.

BLAST Search Results for the Gene(s) Coding for the SQNFPGSQK (SEQ ID NO: 25) and RLSNRLLLR (SEQ ID NO: 12) Peptides Homology searches of SQNFPGSQK (SEQ ID NO: 25) in the public non-redundant human protein database yielded no exact matches, although the seven N-terminal amino acids of the peptide had an exact match in the Pmel17/gp100 sequence (residues 87-95). Nucleotide sequencing of the Pmel17/gp100 RT-PCR product from VMM18 cells yielded an exact match to the published sequence in this region, with no evidence of heterogeneity at these codons (data not shown), suggesting that the sequence does not arise as the result of a mutation or rearrangement of the Pmel17/gp 100 gene. A homology search of the RLSNRLLLR (SEQ ID NO: 12) peptide yielded three exact matches: (i) AE003619, a *drosophila melanogaster* genomic scaffold gene; (ii) AC106771, *Homo sapiens* chromosome 5 clone RP11-308B16; and (iii) AC106790, *Homo sapiens* chromosome 5 clone RP11-376E20. The human sequences are overlapping clones, and in both cases the sequence coding for the RLSNRLLLR (SEQ ID NO: 12) peptide is immediately followed by a stop codon, suggesting that the peptide might occur at the C-terminal end of a protein expressed from a gene coded for in these two clones. To determine if such a gene was expressed in VMM18, PCR primers were designed to amplify a region of DNA that would encompass that coding for the RLSNRLLLR (SEQ ID NO: 12) peptide, as well as sequence immediately 5' to that region. Two primer sets (RLS-F-180/RLS-R-331 and RLS-F-216/RLS-R-331) respectively amplified the predicted 152 bp and 116 bp fragments from both VMM12 and VMM18 cDNA (data not shown), thus confirming that a gene encompassing this region was expressed in melanoma tumor cell lines known to express the peptide.

Identification of the Gene Coding for the Source Protein Containing the RLSNRLLLR (SEQ ID NO: 12) Peptide The GeneRacer™ method of 5' prime RACE was chosen as it ensures the amplification of full-length mRNA by directing the ligation of GeneRacer™ RNA Oligo to mRNA that has not been truncated at the 5' end. PCR was performed with the GeneRacer™ 5' Primer and the 3' reverse primer, RLS-R-119, that was designed to overlap partially the nucleotide sequence coding for the RLSNRLLLR (SEQ ID NO: 12) peptide. An ~200 bp fragment was obtained, cloned into pCR4-TOPO, and sequenced. A BLAST search of the obtained sequence demonstrated that it was completely homologous to AC106771 and overlapped with the sequence obtained from the 152 and 116 bp fragments. The 5' end of the insert read directly into the complete GeneRacer™ RNA Oligo sequence, thus confirming that the complete 5' end of the gene had been obtained.

3' RACE was then used to obtain 3' sequence information for the RLSNRLLLR(SEQ ID NO: 12)-coding gene. The two sets of primers yielded two dominant fragments each, and the difference in the size of the fragments between the two primer sets corresponded to the predicted size difference based on the location of the 5' GSP. The fragments were cloned into pCR4-TOPO and sequenced. A total of four different sequences were obtained for the 3' end of the gene. The 3' end of the sequences corresponded to the GeneRacer™ Oligo dT primer, thus indicating that the 3' primer end of the genes had been obtained.

Example 2

Characterization of the TAG Genes

Gene Structure

By combining the 5' and 3' sequence information, a total of four different isoforms of the gene could be constructed, TAG-1, TAG-2a, TAG-2b, and TAG-2c (FIG. 3). These sequences were further confirmed by sequencing clones obtained following RT-PCR with primers specific for the 5' and 3' end of each isoform. The isoforms are composed of three to four exons each, with each having the α1 and α2 exons in common at the 5' end of the gene. BLAST searches indicate that the genes are coded for on the short arm of Chromosome 5, and have 100% identity to sequences in clones AC106771, AC106790, and AC119151. The seven identified exons span approximately 230,000 nucleotides in the genomic sequence (FIG. 4). Appropriate splice sites exist at each of the intron/exon boundaries to allow splicing of the exons to occur. During the course of sequencing clones that corresponded to TAG-2c, an additional isoform (TAG-3) was isolated that lacked the α2 exon and was composed of the α1, α4, and α7 exons. The splicing of the α1 exon to the α4 exon changed the nucleotide sequence such that the carboxy-terminal Arg in the RLSNRLLLR (SEQ ID NO: 12) peptide was replaced by a Ser (RLSNRLLLS; SEQ ID NO: 46). Although no significant open reading frame initiated from an AUG codon exist exists within the sequences, there are three non-standard initiation codons (two CUG and one ACG), all of which are in frame with one another, and all of which initiate an open reading frame that would code for the peptide (FIG. 3). The sequence coding for the RLSNRLLLR (SEQ ID NO:

12) peptide spans the junction between the first two exons, with the first 26 nucleotides coming from the α1 exon and the 27th nucleotide coming from the α2 exon.

Protein Structure

Depending upon the initiation codon used, the TAG-1 gene potentially codes for a 99 amino acid (aa) (TAG-1α), a 63 aa (TAG-1β), and 59 aa peptide (TAG-1γ), with respective molecular weights of 10,615 D, 6,945 D, and 6,577 D While the TAG-2a, TAG-2b, and TAG-3b genes differ from one another in their fourth exon, all of them potentially express identical proteins as the stop codon is located in the third exon. These genes would use the same initiation codons as in the TAG-1 gene, but would differ from the TAG-1 gene at their 3' end. The expressed proteins would be 93 (TAG-2α), 57 (TAG-2β), and 53 (TAG-2γ) aa in length, with molecular weights of 9,727 D, 6,057 D, and 5,689 D. The TAG-1 protein isoforms, but not the TAG-2 protein isoforms, contain the sequence Asn-Ser-Thr and thus could potentially exist in a glycosylated form. The TAG-1 isoforms have three cysteines and TAG-2 isoforms have four cysteines, which could lead to interchain or intrachain disulfide bond formation. A BLAST search of the TAG-1 and TAG-2 protein isoforms does not reveal any significant homology with known proteins.

Expression of the TAG-1, -2a, -2b, and 2c Genes in Melanoma Tumor Lines

PCR reactions specific for each of the TAG-1, -2a, -2b, and -2c genes were performed on cDNA obtained from 32 established melanoma lines (Table 1). Products were visualized on ethidium bromide stained agarose gels. Screening was initially performed with 30 rounds of amplification with (+) product being easily visualized; (+/−) product cousl be visualized, but the band was very light; (*) product visible only following 40 rounds of amplification; (−) product not visible after 30 or 40 rounds of PCR amplification. When comparing the expression of the four genes in any given tumor line, TAG-1 and -2a were expressed at the highest levels, TAG-2b was poorly expressed, and TAG-2c was expressed at an intermediate level. With the exception of EB81-Mel, each tumor line expressed all four genes or none at all. In the case of EB81-Mel, the TAG-1, -2a, and -2b genes were only seen following 40 cycles of amplification. Overall, TAG-1, 2a, and -2b are expressed in 88% of the melanoma lines tested, while TAG-2c is expressed in 84% of the melanoma lines tested. To ensure that the expression of the TAG gene family was not an artifact of in vitro culture conditions, mRNA was prepared from a cryopreserved aliquot of the original tumor sample from which the VMM12 tumor line was established. RT-PCR was positive for each of the TAG genes, thus establishing that TAG is expressed in uncultured melanoma cells (data not shown). TAG-3 appears to be barely detectable in some, but not all of the melanoma samples.

TABLE 1

Expression of TAG-1, TAG-2a, TAG-2b, and TAG-2c in Established Melanoma Cell Lines[a]

| Tissue | TAG-1 | TAG-2a | TAG-2b | TAG-2C |
|---|---|---|---|---|
| A375 | + | + | + | + |
| AVL3-MEL | + | + | + | + |
| DM6 | + | + | +/− | +/− |
| DM13 | + | + | +/− | + |
| DM14 | + | + | * | +/− |
| DM93 | + | + | +/− | + |
| DM122 | − | − | − | − |
| DM281 | + | + | + | + |
| DM319 | + | + | +/− | + |
| DM331 | + | + | + | + |
| EB81-Mel | * | * | * | − |
| HT144 | + | + | + | + |
| LB373-Mel | + | + | +/− | + |
| Na8-Mel | − | − | − | − |
| SK-Mel-2 | + | + | + | + |
| SK-Mel-5 | + | + | +/− | + |
| SK-Mel-28 | + | + | + | + |
| VMM1 | + | + | + | + |
| VMM5 | + | + | + | + |
| VMM12 | + | + | + | + |
| VMM15 | + | + | + | + |
| VMM17 | + | + | + | + |
| VMM18 | + | + | + | + |
| VMM19 | + | + | + | + |
| VMM34 | + | + | + | + |
| VMM39 | +/− | − | − | − |
| VMM64 | + | + | + | + |
| VMM86 | + | + | +/− | + |
| VMM105 | − | − | − | − |
| VMM150 | + | + | + | + |
| VMM273 | + | + | +/− | + |
| VMM330 | + | + | +/− | +/− |
| Total Positive[b] | 29/32 | 28/32 | 28/32 | 27/32 |
| % Positive | (91%) | (88%) | (88%) | (84%) |

[a]PCR was performed as described in Materals and Methods. (+) product was easily visualized; (+/−) product could be visualized, but the band was very light; (−) product not visible.
[b]Melanoma lines are considered positive if a band is observed after 30 or 40 rounds of PCR amplification, or both.

Expression of the TAG-1, -2a, -2b, and 2c Genes in Transformed and Malignant Leukocyte-derived Cell Lines RT-PCR of mRNA derived from multiple B-LCL and from the hybrid T-B LCL, T2-A3, demonstrates that the TAG gene family is not expressed in transformed B or T cells (Table 2). All four TAG genes were, however, expressed in K562, a myelogenous leukemia cell line (Table 2). PCR products were visualized on ethidium bromide stained agarose gels. Screening was initially performed with 30 rounds of amplification with (+) product being easily visualized; (+/−) product cousl be visualized, but the band was very light; (−) product not visible after 30 or 40 rounds of PCR amplification.

Expression of the TAG-1, -2a, -2b, and 2c Genes in Normal Tissue

The expression of the TAG family of genes was determined in mRNA derived from normal tissues (Table 3). Products were visualized on ethidium bromide stained agarose gels. Screening was initially performed with 30 rounds of amplification with (+) product being easily visualized after 30 rounds of amplification (*) product visible only following 40 rounds of amplification; (−) product not visible after 30 or 40 rounds of PCR amplification. The results demonstrated that with the exception of the testis and placenta, the TAG genes are not expressed in normal tissue. The expression of TAG-1 can be seen in the placenta following 30 cycles of amplification, and TAG-2a is weakly detectable. Upon 40 cycles of amplification, TAG-1, -2a, and -2b are easily detected in placenta, but TAG-3b is not visualized. TAG-1 and -2a expression is readily observed in the testis following 30 cycles of amplification, and all four genes are detectable following 40 cycles of amplification. The expression of the TAG genes in testis and placenta, but not in other normal tissues indicates that they share expression profiles with other cancer/testis antigens.

TABLE 2

Expression of TAG-1, TAG-2a, TAG-2b, and TAG-2c in Non-Melanoma Cell Lines[a]

| Cell Line | Cell Type | TAG-1 | TAG-2a | TAG-2b | TAG-2c |
|---|---|---|---|---|---|
| C1R-A3 | B-LCL | − | − | − | − |
| JY | B-LCL | − | − | − | − |
| VMM12-EBV | B-LCL | − | − | − | − |
| VMM15-EBV | B-LCL | − | − | − | − |
| VMM18-EBV | B-LCL | − | − | − | − |
| T2-A3 | Hybrid B/T-LCL | − | − | − | − |
| K562 | Myelogenous Leukemia | + | + | +/− | + |

[a]PCR was performed as described in Materals and Methods. (+) product was easily visualized; (+/−) product could be visualized, but the band was very light; (−) product not visible.

TABLE 3

Expression of TAG-1, TAG-2a, TAG-2b, and TAG-2c in Normal, Human Tissue[a]

| Tissue | TAG-1 | TAG-2a | TAG-2b | TAG-2c |
|---|---|---|---|---|
| Adrenal | − | − | − | − |
| Bladder | − | − | − | − |
| Brain, Cerebellum | − | − | − | − |
| Brain, Whole | − | − | − | − |
| Breast | − | − | − | − |
| Colon with Mucosal Lining | − | − | − | − |
| Esophagus | − | − | − | − |
| Fetal Brain | − | − | − | − |
| Fetal Liver | − | − | − | − |
| Heart | − | − | − | − |
| Kidney | − | − | − | − |
| Liver | − | − | − | − |
| Lung | − | − | − | − |
| Ovary | − | − | − | − |
| Pancreas | − | − | − | − |
| PBMC | − | − | − | − |
| Placenta | + | + | * | − |
| Prostate | − | − | − | − |
| Salivary Gland | − | − | − | − |
| Skeletal Muscle | − | − | − | − |
| Skin | − | − | − | − |
| Small Intestine | − | − | − | − |
| Spinal Cord | − | − | − | − |
| Spleen | − | − | − | − |
| Stomach | − | − | − | − |
| Testis | + | + | * | * |
| Thymus | − | − | − | − |
| Trachea | − | − | − | − |
| Uterus | − | − | − | − |

[a]PCR was performed as described in Materals and Methods. (+) product was easily visualized at 30 rounds of amplification; (−) product was not visible after 30 or 40 rounds of amplification; (*) product visible following 40 rounds of amplification, but not following 30 rounds of amplification.

BLAST Search of the TAG Genes in the Human EST Database

A BLAST search of the TAG genes against the GenBank Human EST database yielded homology with two chronic myelogenous leukemia (CML) sequences and one hepatocellular carcinoma sequence. CML clone, BF210037, has 96% identity of a 603 bp sequence with the α1, α2, and α3 exons of TAG-1, while CML clone, BF240333, has a 191 bp region out of 741 bp that is 94% identical to the α1 exon of TAG-1, -2a, -2b, and -2c through the first eighteen nucleotides coding the RLSNRLLLR (SEQ ID NO: 12) peptide, after which the sequences diverge. The hepatocellular carcinoma clone, AV695059, has a 272 bp region out of 421 bp that is 98% identical with the TAG α1 exon and all but the last 3 bp of the α2 domain, after which the sequence diverges. These results demonstrate that the TAG genes may be expressed in a variety of tumors, and that there may be additional isoforms that we have not yet identified.

Expression of the TAG-1, -2a, -2b, and -2c Genes in Tumors of Other than Melanocyte Origin The expression of the TAG family of genes was determined in mRNA derived from a variety of cancer cell lines and/or fresh cancer tissue (Table 4). The results demonstrated that at least one isoform of the TAG genes was expressed in lung, breast, ovarian, colon, gastric and prostate carcinomas. Expression was not observed in brain tumors, pharyngeal squamous carcinoma, tongue squamous cell carcinoma, and cervical squamous cell carcinoma. With only one to four samples of each of the latter cancers tested, it is possible that expression would be observed in a fraction of the samples with a larger sampling. These results show that the TAG genes are expressed in a variety of cancers in addition to melanoma.

TABLE 4

Expression of TAG-1, TAG-2a, TAG-2b, and TAG-2c in Various Human Cancers

| Cancer | PCR Cycles | Number and Percent of Cancers Expressing the TAG Genes | | | |
|---|---|---|---|---|---|
| | | TAG-1 | TAG-2a | TAG-2b | TAG-2c |
| Lung | 30 | 4/9 (44%) | 3/9 (33%) | 2/9 (22%) | 2/9 (22%) |
| | 40 | 6/9 (67%) | 7/9 (78%) | 4/9 (44%) | 4/9 (44%) |
| Breast | 30 | 1/8 (13%) | 1/8 (13%) | 1/8 (13%) | 1/8 (13%) |
| | 40 | 6/8 (75%) | 1/8 (13%) | 1/8 (13%) | 1/8 (13%) |
| Ovarian | 30 | 1/3 (33%) | 1/3 (33%) | 1/3 (33%) | 1/3 (33%) |
| | 40 | 2/3 (67%) | 2/3 (67%) | 2/3 (67%) | 1/3 (33%) |
| Colon | 30 | 2/5 (40%) | 2/5 (40%) | 0/5 (0%) | 0/5 (0%) |
| | 40 | 5/5 (100%) | 4/5 (80%) | 2/5 (40%) | 2/5 (40%) |
| Brain | 30 | 0/4 (0%) | 0/4 (0%) | 0/4 (0%) | 0/4 (0%) |
| | 40 | 3/4 (75%) | 2/4 (50%) | 0/4 (0%) | 2/4 (50%) |
| Gastric | 30 | 3/9 (33%) | 1/9 (11%) | 1/9 (11%) | 1/9 (11%) |
| | 40 | 3/9 (33%) | 1/9 (11%) | 1/9 (11%) | 1/9 (11%) |
| Pharyngeal, Tongue, Cervical | 30 | 0/3 (0%) | 0/3 (0%) | 0/3 (0%) | 0/3 (0%) |
| | 40 | 2/3 (67%) | 0/3 (0%) | 0/3 (0%) | 0/3 (0%) |
| Prostate | 35 | 4/8 (50%) | 1/8 (13%) | 1/8 (13%) | 0/8 (0%) |

The invention claimed is:

1. An isolated nucleic acid sequence comprising the sequence of SEQ ID NO: 1.

2. The nucleic acidسیquence of claim 1 wherein said nucleic acid sequence is labeled, either directly or indirectly with a detectable label.

3. A recombinant construct, said construct comprising a non-native promoter operably linked to the nucleic acid sequence SEQ ID NO: 1.

* * * * *